US012167732B2

United States Patent
(12) United States Patent
Henry et al.

(10) Patent No.: US 12,167,732 B2
(45) Date of Patent: Dec. 17, 2024

(54) ALKALI-RESISTANT CALCIUM PHOSPHATE/NUCLEIC ACIDS HYBRID CARRIER FOR PEST CONTROL AND METHOD TO PRODUCE THE PARTICLES

(71) Applicant: CORNING INCORPORATED, Corning, NY (US)

(72) Inventors: David Henry, Fontaine le Port (FR); Valerie Claudine Lacarriere, Larchant (FR)

(73) Assignee: CORNING INCORPORATED, Corning, NY (US)

( * ) Notice: Subject to any disclaimer, the term of this patent is extended or adjusted under 35 U.S.C. 154(b) by 670 days.

(21) Appl. No.: 17/110,389

(22) Filed: Dec. 3, 2020

(65) Prior Publication Data

US 2021/0169083 A1 Jun. 10, 2021

Related U.S. Application Data

(60) Provisional application No. 62/945,780, filed on Dec. 9, 2019.

(51) Int. Cl.

| | |
|---|---|
| *A01N 57/16* | (2006.01) |
| *A01N 25/04* | (2006.01) |
| *A01N 63/60* | (2020.01) |
| *C12N 15/11* | (2006.01) |
| *C12N 15/113* | (2010.01) |

(52) U.S. Cl.

CPC ............ *A01N 57/16* (2013.01); *A01N 25/04* (2013.01); *C12N 15/113* (2013.01)

(58) Field of Classification Search
CPC ........ A01N 57/16; A01N 63/60; A01N 25/04; C12N 15/113; C12N 15/111; C12N 2310/14; C12N 2320/32
See application file for complete search history.

(56) References Cited

U.S. PATENT DOCUMENTS

| | | | |
|---|---|---|---|
| 8,841,272 | B2 | 9/2014 | Zhu et al. |
| 8,906,876 | B2 | 12/2014 | Raemaekers et al. |
| 10,226,424 | B2 | 3/2019 | Parette et al. |

(Continued)

FOREIGN PATENT DOCUMENTS

| | | | |
|---|---|---|---|
| EP | 3116312 | A1 | 1/2017 |
| WO | 2012/143542 | A1 | 10/2012 |
| WO | 2015/089543 | A1 | 6/2015 |

OTHER PUBLICATIONS

Neuhaus et al, Gene silencing of the pro-inflammatory cytokine TNF-α with siRNA delivered by calcium phosphate nanoparticles, quantified by different methods, 2015, J. Mater. Chem. B, 3, 7186-7193. (Year: 2015).*

(Continued)

*Primary Examiner* — Trevor Love
(74) *Attorney, Agent, or Firm* — Svetlana Z. Short

(57) ABSTRACT

A stable aqueous suspension includes a composition which includes nanoparticles, wherein said nanoparticles include a nucleic acid at least partially encapsulated in a matrix comprising calcium phosphate. The nanoparticle compositions and suspensions have high nucleic acid loading and high stability, and may be used for protecting crops against insects and for down-regulating expression of a target gene in an insect pest species in order to prevent and/or control pest infestation.

25 Claims, 14 Drawing Sheets

(56) References Cited

U.S. PATENT DOCUMENTS 10,405,539 B2    9/2019    Mitter et al.
2006/0062855 A1  3/2006    Bell

OTHER PUBLICATIONS

Kelly et al, Scaffold-Based Delivery of Nucleic Acid Therapeutics for Enhanced Bone and Cartilage Repair, May 2019, J. Ortho. Res., 37:1671-1680. (Year: 2019).*

Levingstone et al, Calcium Phosphate Nanoparticles for Therapeutic Applications in Bone Regeneration, Nov. 2019, Nanomaterials, 9(11), 1570, pp. 1-30. (Year: 2019).*

Li et al, Biodegradable calcium phosphate nanoparticle with lipid coating for systemic siRNA delivery, 2009, J. Cont. Rel., 142 (2010) 416-421. (Year: 2009).*

Graham et al., "A new technique for the assay of infectivity of human adenovirus 5 DNA" Virology, vol. 52, Issue 2, Apr. 1973, pp. 456-467.

Jordan et al., "Transfecting mammalian cells: optimization of critical parameters affecting calcium-phosphate precipitate formation" Nucleic Acids Research, vol. 24, No. 4, 1996, pp. 596-601.

Julian A.T. Dow, "pH Gradients in Lepidopteran Midgut", J exp Biol, vol. 172, 1992, pp. 355-375.

Rodrigues et al., "Management of Insect Pest by RNAi—A New Tool for Crop Protection" 2016.

Sokolova et al., "Effective transfection of cells with multi-shell calcium phosphate-DNA nanoparticles", Biomaterials, vol. 27, 2006, pp. 3147-3153.

Welzel et al., "Transfection of cells with custom-made calcium phosphate nanoparticles coated with DNA" Journal of Materials Chemistry, 2004.

Xu et al., "A facile approach to construct hybrid multi-shell calcium phosphate gene particles", J Zhejiang Univ Sci B., vol. 11, 2010, pp. 292-297.

* cited by examiner

ALKALI-RESISTANT CALCIUM PHOSPHATE/NUCLEIC ACIDS HYBRID CARRIER FOR PEST CONTROL AND METHOD TO PRODUCE THE PARTICLES

CROSS-REFERENCE TO RELATED APPLICATIONS

This application claims the benefit of priority under 35 U.S.C. § 119 of U.S. Provisional Application Ser. No. 62/945,780 filed on Dec. 9, 2019, the content of which is relied upon and incorporated herein by reference to its entirety.

TECHNICAL FIELD

This disclosure relates to compositions for delivery of nucleic acids in to cells or microorganisms. In particular, the disclosure relates to delivery of insecticidal RNA to pests and insects to protect plants and crops.

BACKGROUND

Plant pests and pathogens are estimated to reduce global crop yields by 30 to 40% per year. At the same time chemical control, i.e. use of pesticides, used for decades and considered so far as the best option to control the pest population is now regarded as a potential source of health risks as it can cause a number of severe health effects and illnesses and can poison durably the environment. A second problem resulting from the overuse or misuse of chemical pesticides is the resistance developed by the pest against such chemical agents. It is known that pests having a short generation time develop faster resistance that makes the pesticides rapidly inoperable. The use of transgenic plants expressing insecticidal proteins has been considered as an option but deployment of transgenic plants faced public resistance and might be not compliant with some regulations in certain countries. Consequently, there is a growing need for new approach to crop protection.

RNA interference (RNAi) has been used for years by researchers for genetic research but it was recently demonstrated that RNA interference could be used to silence certain targeted genes within pest. RNAi is a process in which small, 19-30 nucleic acid RNA molecules trigger the destruction or decay of complementary transcripts. RNAi-based pest control improves upon traditional small molecule pesticides by providing high specificity to the target species. Such biological approach appears attractive since a specific pest may be targeted and its population put under control without affecting non-target species, which is impossible using chemical pesticides. For example, it was demonstrated that dsRNAs introduced to mosquito larvae could induce an RNAi-mediated knockdown of male fertility genes. Colorado potato beetle (CPB) population may be put under control using RNA interference by simply spraying the appropriate RNA onto the potato plants foliage.

It is now well recognized that if RNA interference is a promising option, having a way to deliver the RNA molecules to insects remains the chief problem to solve. Ideally, the RNA has to be delivered to the pest, e.g. insect, by a simple oral delivery. However, for oral treatments the dsRNA must survive ingestion then has to be absorbed by the epithelial cells and migrate to the appropriate tissue to activate the RNAi mechanism. Another important issue to be solved comes from the low stability of the RNA molecule in the environment that is rapidly digested by RNAses and can undergo self-cleavage under sunlight. RNAses may be present in the digestive channel of the target insect but also in the environment.

Some previous attempts to used RNAi to control pest involved simple topical applications of naked-RNA devoid of any protection on the plant surfaces, e.g. the leaf surfaces, but such techniques require large amount of nucleic acids since most of them are quickly degraded in the field typically in less than one week which makes the treatment economically not viable. It was estimated that such RNAi-based treatment have to last for at least one month to be economically interesting but to do so the RNA have to be protected against exterior aggressions.

Another problem is that when the targeted pest is an insect, once the RNA has reached the targeted pest it has to resist the harsh environment observed in the gut lumen of the insect. For example, the gut of lepidopteran can exhibit a pH of 10-11, comparable to the one of an oven-cleaner that leads quickly to hydrolysis of the most resistant molecules. In addition, many nucleases are present in the alimentary tract that can also cause degradation of the RNA. As a natural vector, yeasts that express the RNA of interest for RNA interference may be used to feed the targeted pest. However, the yeast are living organisms making complicated the use and storage of the product.

One simple way to protect RNA and to improve its delivery within the cell of the target organism is to form a complex between the negatively charged RNA and some positively charged polycations. The complex is called polyplex and was widely used for transfection for therapeutic applications. Among efficient polycations synthetic PEI or chitosan, derived from naturally occurring chitin, but also guanidine-containing polymers were widely used for that purpose. In order to improve even more the protection against nucleases, it was proposed to use polymers such as dextran sulfate which is known to be an efficient inhibitor of nucleases as most of the sulfated polyanions are nuclease inhibitors (see e.g., U U.S. Pat. No. 8,841,272 B2).

Recently, clay compositions for delivery of double strand RNA to plants which protect the plants against a range of organisms have been proposed. In this approach, the RNA is simply adsorbed on a layered double hydroxide (LDH) clay complex. The composition may be in the form of a suspension which may be sprayable onto the plants (see e.g., European Patent Application No. 3116312). LDHs are mixed hydroxide of divalent and trivalent metals having an excess of positive charges balanced by internal ions and can absorb negatively charged nucleic acids. Although such a combination of nucleic acid and inorganic carrier appears to be very simple to be put in practice, the delivery of the nucleic acid in the appropriate amount might be not so effective. More recently in the U.S. Pat. No. 10,405,539, an improvement of the clay-based technique by pre-treating the clay particles with a polycation as an extra step prior contacting the RNA to increase the electrostatic interactions between the so coated clay and the negatively charged nucleic acids has been reported. Thy reported RNA loading is only 1 wt. % in the solid system when using polyethyleneimine (PEI) pretreatment. Such RNA loading is not high enough for applications, especially plant based application. However, by treating the clay with poly (2-dimethyl aminoethyl methacrylate) (PDMAEMA), a synthetic cationic polymer, they achieved up to 25% RNA loading. Although this improved method enables a higher RNA loading, the method required an extra step of coating using a synthetic polymer.

These results show that absorption of the appropriate amount of nucleic acids onto the surface of inorganic carrier remains challenging and greatly dependent of the polycation used.

In the early 1970s, Graham and van der Eb (*Virology; Volume* 52, Issue 2, April 1973, Pages 456-467) discovered that DNA co-precipitated with the calcium phosphate formed by reaction between, calcium chloride and phosphate buffer and, when contacted to cell, became adsorbed to the cells. This technique was widely used in the last decades to transfect mammalian cell in-vitro and such calcium phosphate inorganic nanoparticles are considered as promising non-viral vectors for gene therapy applications. However, the technique developed by Graham required the use of a large excess of calcium to increase the cell trafficking and thus promotes the nanoparticles internalization and as a result the penetration of the nucleic acid into the cytosol. Typically, in the Graham's protocol, the calcium to phosphate ratio is >200.

The large excess of calcium ions increases the ionic strength which has deleterious effect on the stability of the electrostatically stabilized suspension. Such excess of calcium leads to unstable calcium phosphate/nucleic acid suspensions that undergo rapid aggregation and uncontrolled size increase. The resulting suspensions flocculate and are not stable enough to be stored, actually they have to be use for transfection right after their preparation. Therefore, the method reported by Graham and those from many other authors relying on a high calcium to phosphate ratio cannot be used to prepare stable suspensions that may be stored as it is required for phytosanitary compositions. In another example, M Jordan et al. in "Transfecting mammalian cells: optimization of critical parameters affecting calcium-phosphate precipitate formation," 96-601 Nucleic Acids Research, 1996, Vol. 24, No. 4, reported that soluble DNA in the reaction mix may be bound into an insoluble complex with calcium phosphate in less than 1 min but extending the reaction time to 20 min results in uncontrolled aggregation and/or growth.

Therefore, there is a need for compositions and methods to prepare stable suspension of CaP/Nucleic acid hybrid nanoparticles having a high nucleic acid loading to avoid spraying high amounts of inorganics on crops to reach the amount of RNA required to control the pest by RNA interference, or to administer too high amounts to animals to be effective.

SUMMARY

According to a first aspect, a composition comprises nanoparticles, wherein said nanoparticles comprise a nucleic acid at least partially encapsulated in a matrix comprising calcium phosphate. In certain embodiments, the nucleic acid at least partially encapsulated in a calcium phosphate matrix comprises ribonucleic acid, deoxyribonucleic acid, or derivatives thereof. In certain embodiments, the composition further comprises a capping agent at least partially coating the nanoparticle or permeating the nanoparticle or both.

In certain embodiments, the capping agent comprises a polycation. In certain embodiments, the polycation is selected from the group consisting of polyamines, polylysine, polyarginine, polyornithine, polyalkyleneimine, chitosan, oligopeptides, cationized polysaccharides, cationized vegetal proteins or cationized animal proteins, protamines, diethylaminoethyl-dextran, polyamidoamines, poly(beta-aminoesters), aminopolysaccharides polypropylenimine, polyallylamine, polyvinylamine homo- or copolymer, poly (vinylpyridin), homo- or copolymer, poly (meth)acrylate homo- or copolymer, poly(meth)acrylamide homo- or copolymer, and derivatives thereof. In certain embodiments, the polycation is polyethyleneimine.

In certain embodiments, the nanoparticles have a peak particle size of less than 500 nm. In certain embodiments, the nanoparticles have a peak particle size range of 50 nm to 500 nm. In certain embodiments, the weight ratio of calcium phosphate to nucleic acid in the nanoparticle is from 100:1 to 1:1.5. In certain embodiments, the weight ratio of calcium phosphate to nucleic acid to capping agent in the nanoparticle is from 2:1:2 to 2:5:2. In certain embodiments, the ratio of number of positively charged nitrogen atoms of the polycation to the number of phosphorus atoms of the nucleic acid is greater than 1. In certain embodiments, the nanoparticles are suspended in an aqueous dispersion having a pH of 6 to 11. In certain embodiments, the nanoparticles are suspended in an aqueous dispersion having a pH of 7 to 8. In certain embodiments, the composition is a stable aqueous suspension.

According to a second aspect, a stable aqueous suspension comprises a composition comprising nanoparticles, wherein the nanoparticle comprises a nucleic acid at least partially encapsulated in a matrix comprising calcium phosphate. In certain embodiments of the stable aqueous suspension, the composition further comprises a capping agent at least partially coating the nanoparticle or permeating the nanoparticle or both. In certain embodiments, the nucleic acid loading is from about 0.1 wt. % to about 50 wt. % with respect to the total mass of the nanoparticles. In certain embodiments, the concentration of calcium phosphate in the aqueous suspension is less than 100 μg/ml. In certain embodiments, the molar ratio of calcium to phosphorous in the calcium phosphate suspension is from 1.5:1 to 5:1. In certain embodiments, the suspension is alkali-resistant. In certain embodiments, the stable aqueous suspension further comprises an additive selected from the group consisting of nuclease inhibitors, surfactants, wetting agents, UV absorbers, antioxidant, antifreeze agents, preservatives, coloring agents, insecticides, fungicides, attractants, repellent, and rheology modifiers.

According to a third aspect, a method of protecting a crop against an insect, the method comprises administering the composition to the crop, wherein the composition comprises nanoparticles, wherein said nanoparticles comprise a nucleic acid at least partially encapsulated in a matrix comprising calcium phosphate. In certain embodiments, the nucleic acid at least partially encapsulated in a calcium phosphate matrix comprises ribonucleic acid, deoxyribonucleic acid, or derivatives thereof. In certain embodiments, the composition further comprises a capping agent at least partially coating the nanoparticle or permeating the nanoparticle or both. In certain embodiments, the composition is administered to the crop by spraying, drip-feeding, or irrigation. In certain embodiments, the nucleic acid in the composition comprises insecticidal double stranded ribonucleic acid. In certain embodiments, the method includes protecting a crop against hemiptera, coleoptera, siphonaptera, dichyoptera, lepidoptera, orthoptera and diptera.

According to a fourth aspect, a method for producing hybrid nanoparticles comprises adding a nucleic acid to one of a calcium salt solution or a phosphoric acid salt solution in a reactor; adjusting the pH of said calcium and phosphoric acid salt solutions to about 6 to about 9; and mixing said calcium salt solution with said phosphoric acid salt solution to form calcium phosphate-nucleic acid hybrid nanoparticles. In certain embodiments, the method further comprises adding a polycation solution to said mixed solution. In certain embodiments, the calcium salt is selected from a group consisting of calcium chloride, calcium nitrate, calcium acetate and calcium lactate. In certain embodiments, the phosphoric acid salt is selected from a group consisting of trisodium phosphate, tripotassium phosphate, potassium hydrogen phosphate, sodium hydrogen phosphate, ammonium phosphate, and ammonium hydrogen phosphate. In certain embodiments, the nucleic acid is at least partially encapsulated in the calcium phosphate nanoparticles. In certain embodiments, the hybrid nanoparticles have a peak particle size range of 50 nm to 500 nm. In certain embodiments, the pH of the calcium salt solution is about 7.5. In certain embodiments, the pH of the phosphate salt solution is about 7.5. In certain embodiments of the method, the reactor is selected from the group consisting of a batch reactor, a semi-batch reactor, a continuous flow reactor, an advanced flow reactor, a fluidized bed reactor and a combination thereof.

According to a fifth aspect, a method for preparing a suspension of hybrid nanoparticles in a continuous flow reactor comprises adding a nucleic acid to one of a calcium salt solution or a phosphoric acid salt solution; flowing the calcium salt solution into a first inlet of a flow reactor; flowing the phosphoric acid salt solution into a second inlet of the flow reactor so as to mix the phosphoric acid salt solution stream with the calcium salt solution stream and produce a calcium phosphate-nucleic acid hybrid nanoparticle stream flowing from said reactor; collecting and processing the suspension comprising calcium phosphate-nucleic acid hybrid nanoparticles from the reactor. In certain embodiments, the method further comprises flowing a capping polymer solution into a third inlet of the flow reactor so as to mix the capping polymer stream with the calcium phosphate stream to produce a polymer capped, nucleic acid encapsulated calcium phosphate stream flowing from said reactor. In certain embodiments, the method further comprises collecting and processing the polymer capped, nucleic acid encapsulated calcium phosphate from the reactor. In certain embodiments, the nanoparticles have a zeta potential of −50 to 50 millivolts. In certain embodiments, the nanoparticles have a mean particle size ranging from 30 nm to 250 nm. In certain embodiments, the nanoparticles are suspended in a liquid medium. In certain embodiments, the liquid medium is selected from the group consisting of water, alcohol, hydrocarbon, and oil.

According to a sixth aspect, a water-in-oil emulsion (W/O) comprises a composition comprising nanoparticles, wherein said nanoparticles comprise a nucleic acid at least partially encapsulated in a matrix comprising calcium phosphate. In certain embodiments, the nucleic acid at least partially encapsulated in a calcium phosphate matrix comprises ribonucleic acid, deoxyribonucleic acid, or derivatives thereof. In certain embodiments, the composition further comprises a capping agent at least partially coating the nanoparticle or permeating the nanoparticle or both.

According to a seventh aspect, a water-in-oil-in water double emulsion (W/O/W) comprises a composition comprising nanoparticles, wherein said nanoparticles comprise a nucleic acid at least partially encapsulated in a matrix comprising calcium phosphate. In certain embodiments, the nucleic acid at least partially encapsulated in a calcium phosphate matrix comprises ribonucleic acid, deoxyribonucleic acid, or derivatives thereof. In certain embodiments, the composition further comprises a capping agent at least partially coating the nanoparticle or permeating the nanoparticle or both.

According to an eight aspect, a glass container which includes the compositions and aqueous suspensions comprising nanoparticles, wherein said nanoparticles comprise a nucleic acid at least partially encapsulated in a matrix comprising calcium phosphate.

BRIEF DESCRIPTION OF THE DRAWINGS

The details of one or more implementations of the subject matter described in this specification are set forth in the accompanying drawings and the description below. Other features, aspects, and advantages of the subject matter will become apparent from the description, the drawings, and the claims.

Like reference numbers and designations in the various drawings indicate like elements.

DETAILED DESCRIPTION

Figure 1:
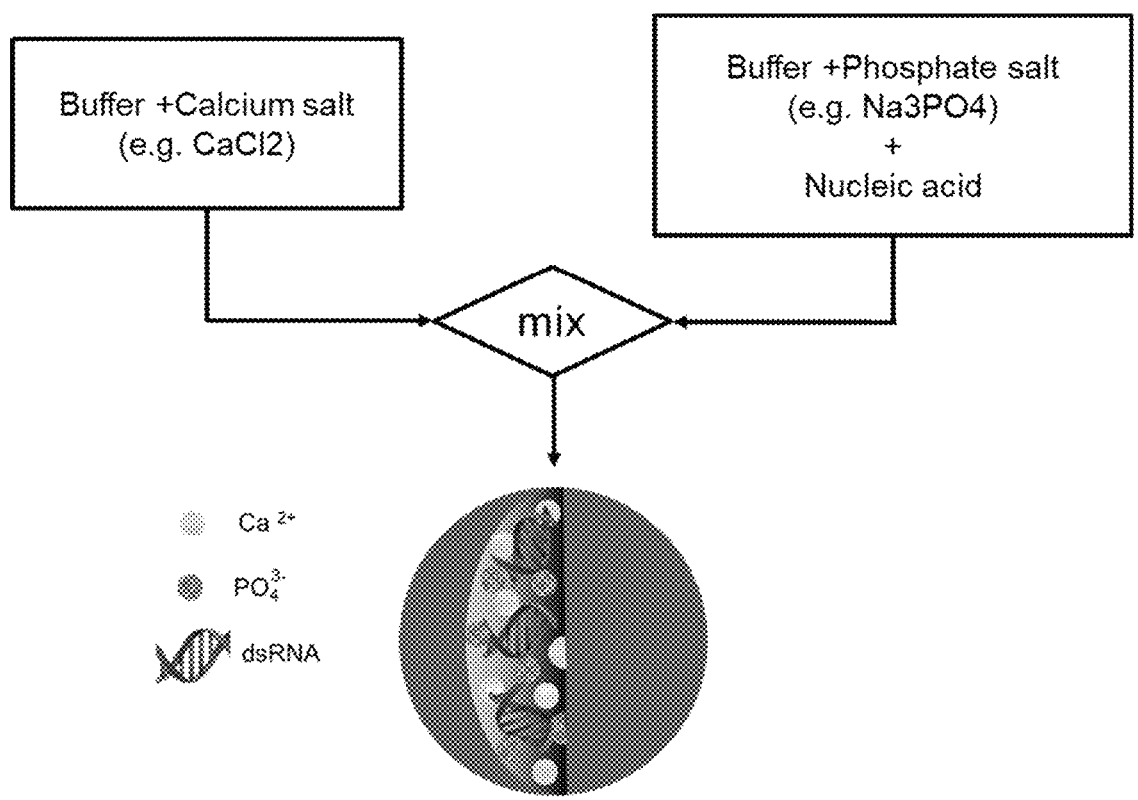
FIG. 1 illustrates a schematic flow diagram of a basic process for preparing the nucleic acid-loaded calcium phosphate nanoparticle (without polycation) and a perspective view of the resulting hybrid nanoparticles in accordance with one or more embodiments shown and described herein.

Reference will now be made in detail to various embodiments which are illustrated in the accompanying drawings. Whenever possible, the same reference numerals will be used throughout the drawings to refer to the same or like parts. The components in the drawings are not necessarily to scale, emphasis instead being placed upon illustrating the principles of the exemplary embodiments.

As discussed above, the present technology generally relates to compositions and methods for the delivery of a desired material, such as nucleic acid, into cells and tissues. In various embodiments, provided herein are compositions and systems including particles, such as nanoparticles, useful for the delivery of therapeutic agents to cells or tissues of plants, animals and insects, and methods for making and using the same.

Definitions

The definitions of certain terms as used in this specification are provided below. Unless defined otherwise, all technical and scientific terms used herein generally have the same meaning as commonly understood by one of ordinary skill in the art to which the present technology belongs.

Definitions

As used in this specification and the appended claims, the singular forms "a", "an" and "the" include plural referents unless the content clearly dictates otherwise. Thus, for example, reference to "a" component includes aspects having two or more such components, unless the context clearly indicates otherwise. For example, reference to "a cell" includes a combination of two or more cells, and the like. Also, the word "or" when used without a preceding "either" (or other similar language indicating that "or" is unequivocally meant to be exclusive—e.g., only one of x or y, etc.) shall be interpreted to be inclusive (e.g., "x or y" means one or both x or y). Generally, the nomenclature used herein and the laboratory procedures in cell culture, molecular genetics, organic chemistry, analytical chemistry and nucleic acid chemistry described below are those well-known and commonly employed in the art.

The term "and/or" shall also be interpreted to be inclusive (e.g., "x and/or y" means one or both x or y). In situations where "and/or" or "or" are used as a conjunction for a group of three or more items, the group should be interpreted to include one item alone, all the items together, or any combination or number of the items. Moreover, terms used in the specification and claims such as have, having, include, and including should be construed to be synonymous with the terms comprise and comprising. Other elements may optionally be present other than the elements specifically identified by the "and/or" clause, whether related or unrelated to those elements specifically identified. As a non-limiting example, a reference to "X and/or Y" can refer, in one embodiment, to X only (optionally including elements other than Y); in some embodiments, to Y only (optionally including elements other than X); in yet some embodiments, to both X and Y (optionally including other elements).

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

"Particle size" as used herein refers to particle diameter unless otherwise stated. The particle size is expressed for example as peak particle size which represents the hydrodynamic diameter of the particles by dynamic light scattering (DLS) techniques. The particle size is also expressed as mean or average particle size.

The present technology relates to a stable aqueous suspension prepared from nucleic acids and precipitated alkali-stable calcium phosphate combined with at least one cationic polymer for delivery of nucleic acid to pest and the method to produce the said aqueous suspension. The methods of the present technology are directed to the spontaneous formation of calcium phosphate nanoparticles from calcium salt and phosphate salt in presence of the nucleic acid to be loaded to yield the stable calcium phosphate/nucleic acid nanoparticles suspension. Additional methods are directed to the overcoating of nucleic acid/calcium phosphate particle with a polycation to provide stability in variable pH conditions, including highly alkaline conditions.

Compositions

Aspects of the present technology relate to compositions and suspensions including nanoparticles. In various embodiments, the nanoparticle includes a matrix including calcium phosphate (CaP). In various embodiments, CaP represents a family of minerals that contains calcium cations and phosphate anions. Exemplary minerals may include, without limitation, hydroxyapatite ($Ca_{10}(PO_4)_6(OH)_2$) or suitable precursors thereof, mono or biphasic calcium phosphates, dicalcium phosphate, tricalcium phosphate, β-tricalcium phosphate (β-$Ca_3PO_4$), composites of calcium sulfate and hydroxyapatite, composites of hydroxyapatite or combinations thereof. Suitable nanoparticle matrix materials include CaP biomaterials which may be used in several pharmaceutical, biomedical, food and cosmetic applications.

The nanoparticle having a calcium phosphate matrix may further include a nucleic acid which is at least partially encapsulated in the matrix. The nucleic acid may be encapsulated within or incorporated into the CaP matrix, may coat or be located on the surface of the CaP matrix, or may both be encapsulated within and coated on the surface of the nanoparticle. Suitable nucleic acids include any ribonucleic acid (RNA) or deoxyribonucleic acid (DNA), which may be unmodified or modified. In various embodiments, nucleic acid includes, without limitation, single- and double-stranded RNA, single- and double-stranded DNA, RNA that is mixture of single- and double-stranded regions, DNA that is a mixture of single- and double-stranded regions, and hybrid molecules comprising DNA and RNA that may be single-stranded or, more typically, double-stranded or a mixture of single- and double-stranded regions. In addition, nucleic acid refers to triple-stranded regions comprising RNA or DNA or both, DNAs or RNAs containing one or more modified bases, and DNAs or RNAs with backbones modified for stability or for other reasons. In some embodiments, the nanoparticles may include other therapeutic agents in addition to the nucleic acid. Suitable nucleic acids and therapeutic agents may be selected from the group consisting of genes, shRNAs, siRNAs, microRNAs, DNA fragments, RNA fragments, plasmids, and combinations thereof. In some embodiments, the nucleic acid includes ribonucleic acid, deoxyribonucleic acid, or derivatives thereof. In some embodiments, the nucleic acid includes ribonucleic acid or derivatives thereof. In other embodiments, the nucleic acid includes deoxyribonucleic acid or derivatives thereof. In some embodiments, the nucleic acid includes interfering ribonucleic acid molecules. In some embodiments, the nucleic acid includes small interfering RNA (siRNA).

The nanoparticle may include a capping agent which at least partially coats or permeates the nanoparticle or both coats and permeates the nanoparticle. In various embodiments, the capping agent may include compounds or compositions which facilitate the delivery of nucleic acid to the cells. For example, the capping agent may include cationic compounds, which are compounds having polar groups that are positively charged at or around physiological pH. It is hypothesized that these compounds facilitate delivery of nucleic acids into the cells because of their ability to neutralize the electrical charge of nucleic acids. Exemplary cationic compounds include, without limitation, polycations, cationic lipids, cationic polymers or mixtures thereof. In various embodiments, the capping agent includes a polycation. The polycation to be used as capping agent may be a synthetic polymer, a naturally occurring polymer or a chemically modified naturally occurring polymer. The polycation suitably has a plurality of positively charged groups at pH between 5 and 11. The charged groups may be selected among alkyl amines (including primary, secondary, tertiary and quaternary amines), imine, guanidium and aromatic amines. The polycation may be branched or linear. For example, in the case of PEI, linear polyethyleneimines (PEI) contain all secondary amines, in contrast to branched PEIs which contain primary, secondary and tertiary amino groups. The pKa of the positively charged amino group may be greater than 7.5, such as greater than 8, greater than 9 or greater than 10. The net cationic charge is maintained under alkaline conditions for certain applications. As a consequence, the nucleic acid remains bound to the polycation which provides some protection against degradation by nucleases (the polycation/nucleic acid complex is known to exhibit a better stability than the uncomplexed form). The polycation may contain one or several type of amino groups having different pKa values. The polycation may be a homopolymer or a copolymer. When the positively charged polymer is a copolymer the comonomer to be copolymerized with the monomer comprising the charge amino group is selected in order to maintain a sufficient level of water solubility to the copolymer. Other water soluble polycations may be selected among chitosan and its derivatives such as trimethyl chitosan, guanidilated chitosan, cationized polysaccharides such as DEAE Dextran and cationized vegetal proteins or cationized animal proteins.

Suitable polycations include, without limitation, polyamines, polylysine, polyarginine, polyornithine, polyalkyleneimine, chitosan, oligopeptides, cationized polysaccharides, cationized vegetal proteins or cationized animal proteins, protamines, activated dendrimers, diethylaminoethyl-dextran, polyamidoamines, poly(beta-aminoesters), aminopolysaccharides polypropylenimine, polyallylamine, polyvinylamine homo- or copolymer, poly(vinylpyridin), homo- or copolymer, poly (meth)acrylate homo- or copolymer, poly(meth)acrylamide homo- or copolymer, and derivatives thereof, cationic compounds that include peptides and protein fragments or combinations thereof. Examples of preferred n is polyethyleneimine (PEI), Hexadimethrine bromide (available under the trade name polybrene), polyhexamethylene guanidine (PHMG), polyhexamethylene biguanidine, polyallylamine, guanidinylated poly(allyl amine), polyaminopropylmethacrylamide, poly-[N-(3-guanidinopropyl)methacrylamide], poly aminoethyl (meth)acrylate, polydimethylaminoethylmethacrylate (PD-MAEMA). In various embodiments, the polycation includes polyethyleneimine.

The amount of polycation may be added in a sufficient amount to convert the negative charge of the CaP/Nucleic acid parent particles into a positively charge particle having surface charge of at least +10 mV, such as at least +20 mV in order to provide an acceptable colloidal stability.

In another aspect, provided herein are suspensions which include the nanoparticle compositions described herein. The stable suspension may include calcium phosphate-nucleic acid nanoparticles suspended in a suitable solvent. Exemplary solvents include water and water-insoluble organic solvents. Exemplary solvents include water, alcohol, hydrocarbon, and oil. In various embodiments, a stable aqueous suspension includes the composition may be a stable aqueous suspension including calcium phosphate nanoparticles described herein. In various embodiments, the suspension may include CaP-nucleic acid nanoparticles suspended in an aqueous dispersion. The stable aqueous suspension may be prepared from nucleic acids and precipitated alkali-stable calcium phosphate.

The aqueous dispersion of the suspension may suitably have a near neutral or alkaline pH. For example, the suspension may include the nanoparticles suspended in an aqueous dispersion having a pH of about 6 to about 11. This includes a pH of about 6 to about 10, about 6 to about 9, about 6 to about 8, about 6 to about 7, about 7 to about 11, about 7 to about 10, about 7 to about 9, about 7 to about 8, 8 to about 11, about 8 to about 10, about 8 to about 9, about 9 to about 11, about 9 to about 10 or about 10 to about 11, or any range including and/or in-between any two of these values. In various embodiments, the suspension may include the nanoparticles suspended in an aqueous dispersion having a pH of about 7 to about 8.

The nanoparticles are unique in that the nucleic acid is entrapped inside the particles as well as adsorbed onto the surface of the particles. Consequently, the nucleic acid loading is much higher and compatible with several applications. The amount of nucleic acid loaded on to the nanoparticle may be higher than that obtained using traditional adsorption methods. In some embodiments, the amount of nucleic acid loaded on to the nanoparticle may be greater than about 0.1 wt. % with respect to the total mass of the nanoparticles. In other embodiments, the amount of nucleic acid loaded on to the nanoparticle may be greater than about 10 wt. % with respect to the total mass of the nanoparticles. In some embodiments, the amount of nucleic acid loaded on to the nanoparticle may be greater than about 20 wt. % with respect to the total mass of the nanoparticles. In various embodiments, the nucleic acid loading in the nanoparticle can range from about 0.1 wt. % to about 55 wt. % with respect to the total mass of the nanoparticles. For example, the nucleic acid loading in the with respect to the total mass of the nanoparticles may be from about 0.1 wt. % to about 50 wt. %, from about 1 wt. % to about 45 wt. %, from about 5 wt. % to about 40 wt. %, from about 10 wt. % to about 35 wt. %, from about 15 wt. % to about 30 wt. %, or from about 20 wt. % to about 20 wt. %, or any range including and/or in-between any two of these values. In various embodiments, the nucleic acid loading in the nanoparticle is from about 0.1 wt. % to about 50 wt. % with respect to the total mass of the nanoparticles.

Although partially flocculated calcium phosphate/nucleic acid nanoparticles suspension can probably be employed in certain applications, stable suspensions, which are exempt of aggregation, are desired for most industrial applications. A stable suspension is preferred to avoid blockage of the delivery equipment and to assure an even deposition and delivery. Accordingly, to avoid flocculation, the concentration of calcium phosphate in the final suspension may be less than 200 µg/ml. For example, the concentration of calcium phosphate in the suspension may be less than about 150 µg/ml, less than about 120 µg/ml, less than about 100 µg/ml, less than about 90 µg/ml, less than about 80 µg/ml, less than about 70 µg/ml, less than about 60 µg/ml, or less than about 50 µg/ml. The concentration of calcium phosphate in the suspension may be from about 1 µg/ml to about 150 µg/ml, from about 10 µg/ml to about 100 µg/ml, from about 20 µg/ml to about 90 µg/ml, from about 30 µg/ml to about 80 µg/ml, from about 40 µg/ml to about 70 µg/ml, or from about 50 µg/ml to about 60 µg/ml, or any range including and/or in-between any two of these values. In various embodiments, the concentration of calcium phosphate in the suspension is less than 100 µg/ml. In various embodiments, the concentration of calcium phosphate in the suspension is less than 50 µg/ml.

The content of calcium with respect to the total phosphate ions (i.e. phosphate of the phosphate salt plus phosphate from the nucleic acid) can influence the stability of the nanoparticles. A slight excess of calcium over the phosphate ions may be desirable to produce stable nanoparticle suspension. However, too much excess of calcium may result in rapid aggregation of the nanoparticles in the suspension. The molar ratio of calcium to phosphorous (Ca/P) in the suspension can range from about 1.5:1 to 5:1, such as about 1.6:1 to 4.5:1, about 1.7:1 to 4:1, about 1.8:1 to 3.5:1, about 1.9:1 to 3:1, or about 2:1 to 2.5:1, or any range including and/or in-between any two of these values. In various embodiments, the molar ratio of calcium to phosphorous in the calcium phosphate suspension is from 1.5:1 to 5:1. In various embodiments, the molar ratio of calcium to phosphorous in the suspension is about 1.7:1.

The suspensions of the present technology not only exhibit high stability, but they are also alkali-resistant. The polycation/nucleic acid complex of the capped nanoparticles is likely to be stable up to the value of the pKa of the polycation. Above the pKa, the complex may dissociates and releases the complexed nucleic acid. Alkali-resistance may be important in applications where the nanoparticles are delivered to the digestive system of insects which is known to be highly alkaline (e.g., pH>9.0) and that the survival of the nucleic acid to such a harsh basic environment remains challenging. The suspensions described herein are advantageously alkali-resistant.

The stable aqueous suspensions may further include additives known in the art and listed herein. Suitable additives include, but are not limited to nuclease inhibitors, surfactants, wetting agents, UV absorbers, antioxidant, antifreeze agents, preservatives, coloring agents, insecticides, fungicides, attractants, repellent, and rheology modifiers. The amount of additives is based on the total weight of the nanoparticles in the suspension, unless mentioned otherwise. When present, the suspension may include from about 0.01 wt. % to about 5 wt. % of additives.

The hybrid nanoparticles of the composition have narrow particle size distributions and optimum hydrodynamic diameter. A narrower range of particle sizes corresponds to a more uniform distribution of particle sizes. The hydrodynamic diameter is generally slightly larger than the geometric diameter of the particle because it includes both the native particle size and the solvation shell surrounding the particle. The nanoparticles have a peak particle size of less than about 500 nm, such as for example less than about 450 nm, less than about 400 nm, less than about 350 nm, less than about 300 nm, less than about 250 nm, less than about 200 nm, less than about 150 nm, less than about 100 nm, or less than about 50 nm. The peak particle size of the nanoparticles can range from about 20 nm to about 500 nm, such as about 50 nm to about 500 nm, about 100 nm to about 400 nm, about 150 nm to about 300 nm, or about 200 nm to about 250 nm, or any range including and/or in-between any two of these values. In various embodiments, the nanoparticles have a peak particle size range of 50 nm to 500 nm. In various embodiments, the nanoparticles have a peak particle size range of 50 nm to 100 nm.

The CaP to nucleic acid ratio used may influence the degree of binding or encapsulation of the nucleic acid as well as the stability of the nanoparticles suspension. In case of a large excess of nucleic acid, it is believed that some nucleic acids remains unbound and the stability of the nanoparticles is reduced. The weight ratio of calcium phosphate to nucleic acid in the nanoparticle ranges from about 100:1 to 1:1.5, including, without limitation, from about 80:1 to 1:1.2, from about 50:1 to 1:1, from about 20:1 to 2:1, or from about 10:1 to 5:1, from about 2:1 to 1:1, or any range including and/or in-between any two of these values. In various embodiments, the CaP to nucleic acid weight ratio is about 2:1. At such a ratio, the calcium phosphate/nucleic acid exhibits high stability and almost all the given nucleic acids may be trapped in the nanoparticles.

For CaP/nucleic acid/capping agent hybrid nanoparticles, the mass loading ratio (payload) expressed in terms of the ratio of the three components is such that all of the nucleic acid is associated with the CaP or the capping agent. Thus for maximum binding of the nucleic acid, the weight ratio of calcium phosphate to nucleic acid to capping agent in the nanoparticle ranges from about 2:1:2 to about 2:5:2, including, without limitation, from about 2:1.5:2 to about 2:4.5:2, from about 2:2:2 to about 2:4:2, from about 2:2.5:2 to about 2:3.5:2, or from about 2:2.7:2 to about 2:3:2, or any range including and/or in-between any two of these values. In various embodiments, the weight ratio of calcium phosphate to nucleic acid to capping agent in the nanoparticle is from about 2:1:2 to about 2:5:2.

In order to provide a sufficiently high positive charge to the particle in order to confer an acceptable colloidal stability to the suspension, the N/P ratio (where N is the number of positively charge nitrogen atoms of the polycation and P the number of nucleic acid phosphorus atoms), may be higher than 1, such as higher than 5 or even higher than 10. Such stability may be achieved when the zeta potential at the final pH is higher than +10 mV, such as higher than +20 mV. In addition to a better suspension stability, the positive charge enables the particles to stick to the negatively charged cell membrane, which may be a prerequisite for the internalization process (endocytosis). In various embodiments, the ratio of number of positively charged nitrogen atoms of the polycation to the number of phosphorus atoms of the nucleic acid is greater than 1.

Although the aqueous suspension described herein may be used as is, it may be also advantageously incorporated in an emulsion or a multiple emulsion. The emulsion may be a water-in-oil emulsion or a multiple emulsion. Examples of multiple emulsion includes double emulsion such a water-in-oil-in-water (W/O/W) emulsion. Other single or multiple emulsions can also be used. W/O/W emulsion indicates a double emulsion in which oil (0) droplets enclosing water (W) droplets are dispersing in water (W). The W/O/W emulsion may be readily diluted with water to deliver the appropriate amount of nucleic acid. Without wishing to be bound by theory, it is hypothesized that the oil droplet enclosing the aqueous suspension can provide additional protection to the nucleic acids against nucleases. Such double emulsions are widely used for biopesticide applications. The final external phase is water and dilution of the product may be simply done by adding more water as diluent. The internal phase containing the particle suspension is protected by the oil intermediate phase. The oil droplets containing the nanoparticle aqueous suspension adhere to the hydrophobic surfaces, for example leaf surfaces in plant or crop applications.

Although the embodiments described herein are with respect to nucleic acid, the nanoparticles may be used to incorporate other suitable therapeutic agents or medicaments which may include any compound or substance which is used to treat or prevent any given disease or disorder or in the regulation of a physiological condition in a human or animal subject. In some embodiments, the therapeutic agent may include an antibiotic, an antifungal, a peptide, a protein, a polymer, or combinations thereof. In some embodiments, the nanoparticles may include therapeutic agents in addition to the nucleic acid incorporated therein.

Methods

A variety of methods may be used to produce the nanoparticles, compositions, suspensions and emulsions described herein. For example, the present technology provides a simple method to prepare a suspension of alkali-resistant calcium phosphate/nucleic acid nanoparticles exhibiting a very high nucleic acid loading, with respect to the total mass of the particles (e.g., from 0.1 to 50 wt. %). The preparation of the suspension relies on a single step process in which a large quantity of nucleic acid is at least partially encapsulated inside the nanoparticles in the course of the calcium phosphate precipitation.

Aspects of the present technology relate to a method for producing nanoparticles of calcium phosphate and nucleic acid without a capping agent. In various embodiments, a method for preparing the nanoparticle includes co-precipitating the calcium phosphate with the nucleic acid. Referring now to FIG. 1, an exemplary schematic flow diagram of a basic process used to prepare a CaP/nucleic acid suspension is illustrated. As shown in the figure, the calcium phosphate may be prepared using calcium salts and phosphate salts known in the art. In various embodiments, the method includes adding a nucleic acid to either a calcium salt solution or a phosphoric acid salt solution, adjusting the pH of either the salt solutions or the mixed solution to a suitable value and mixing the calcium salt solution with said phosphoric acid salt solution to form calcium phosphate-nucleic acid nanoparticles.

The formation of calcium phosphate nanoparticle and the kinetics of CaP particles growth is driven by the concentration of the calcium and phosphate salts, the temperature and the pH. As shown in FIG. 1, the pH of the calcium salt solution and/or the phosphate salt solution, at least one of them having the nucleic acid, may be independently adjusted using a buffer solution prior to mixing. Alternatively, the salt solutions, at least one of them having the nucleic acid may be mixed first and then the pH may be adjusted to the desired value. Accordingly, the co-precipitation process is carried out at a pH higher than 6 and lower than 9, for example at a pH between 7 and 8. If the pH is lower than 6, then only few particles may be obtained whereas at pH exceeding 9, the growth of the particles is likely to be difficult to put under control. In various embodiments, the pH of the calcium salt solution is about 7.5. In various embodiments, the pH of the phosphate salt solution is about 7.5.

The temperature during mixing can range from about 1° C. to 70° C., including without limitation, from about 1° C. to 70° C., from about 5° C. to 60° C., from about 10° C. to 50° C., from about 15° C. to 40° C., or from about 20° C. to 30° C., or any range including and/or in-between any two of these values. The time required for formation of the nanoparticle may range from few seconds to few minutes at room temperature. Suitable reaction or mixing time can range from about 5 s to about 10 min, including, without limitation, from about 8 s to about 5 min, from about 10 s to about 1 min, from about 20 s to about 2 min, or from about 30 s to about 1 min, or any range including and/or in-between any two of these values.

The method thus provides spontaneous formation of calcium phosphate nanoparticles from calcium salt and phosphate salt in presence of the nucleic acid to be loaded to yield a highly stable calcium phosphate/nucleic acid nanoparticles suspension. Nucleic acids present during the formation of calcium phosphate becomes encapsulated in the CaP particles by means of a single step process. In one aspect, the method provides a suspension which includes an aqueous medium in which nanoparticles made of the nucleic acid of interest, e.g. RNA, embedded in calcium phosphate are suspended. Such suspension made of CaP/nucleic acid nanoparticles without any overcoat exhibits a high stability due the negative surface charge of the particles provided by the nucleic acid, and may be delivered or applied to the plant, animal or insect as is.

Figure 2:
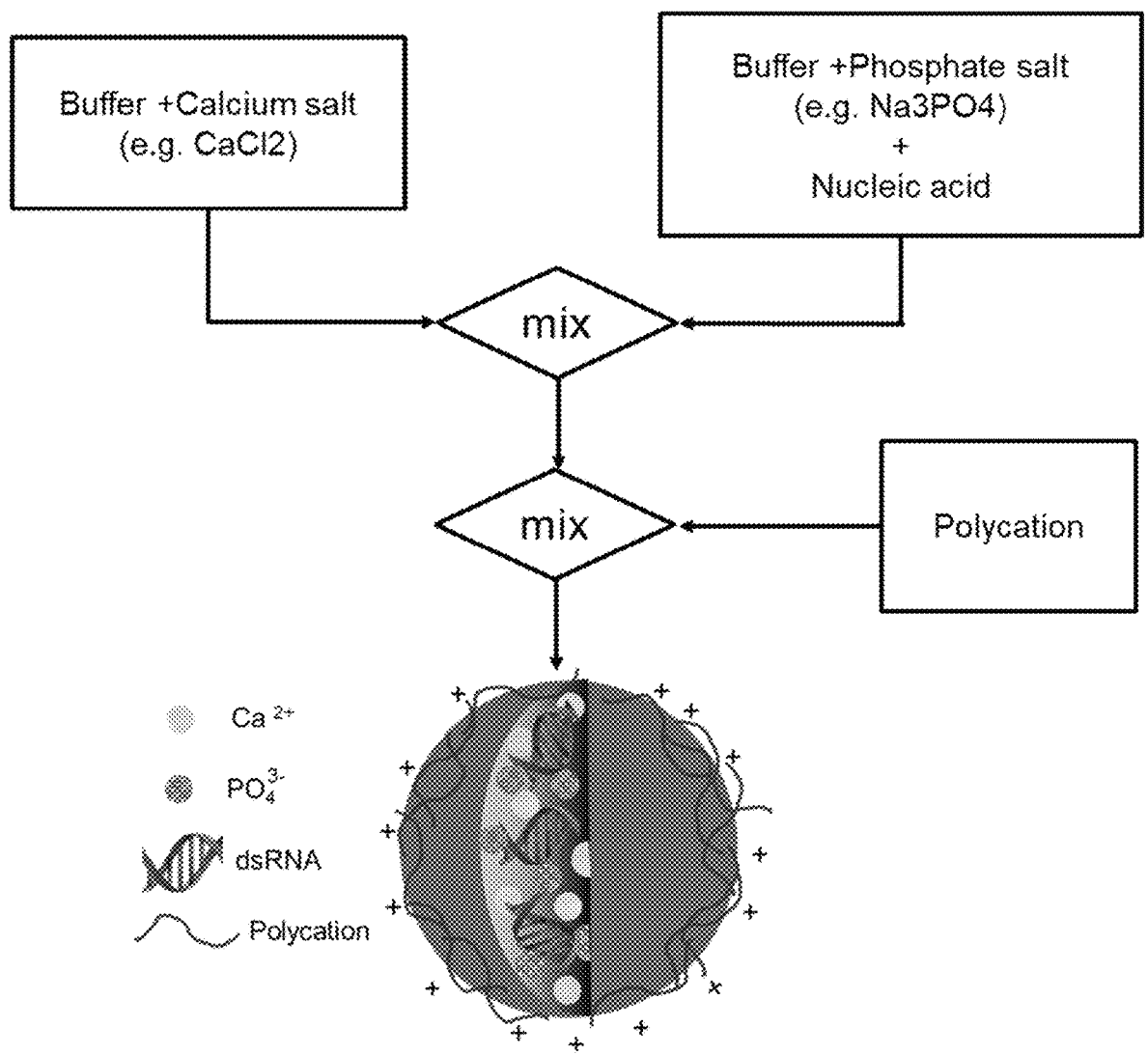
FIG. 2 illustrates a schematic flow diagram of a basic process for preparing the nucleic acid-loaded calcium phosphate nanoparticle with polycation capping and a perspective view of the resulting capped hybrid nanoparticles in accordance with one or more embodiments shown and described herein.
Figure 3:
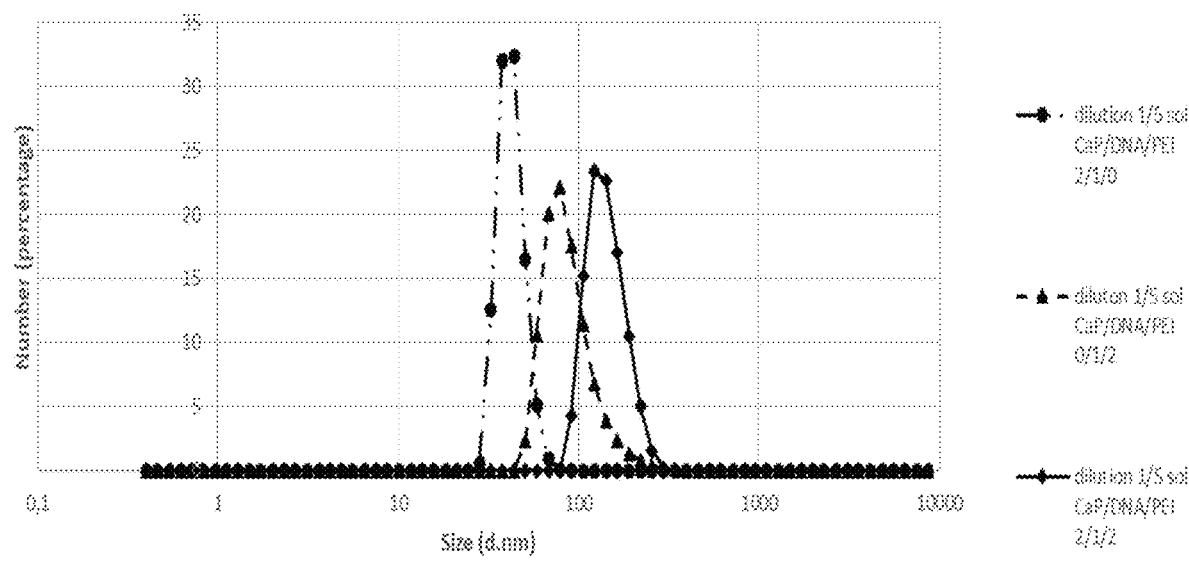
FIG. 3 illustrates a graph showing DLS size of calcium phosphate-DNA nanoparticle particle in accordance with one or more embodiments shown and described herein.
Figure 4:
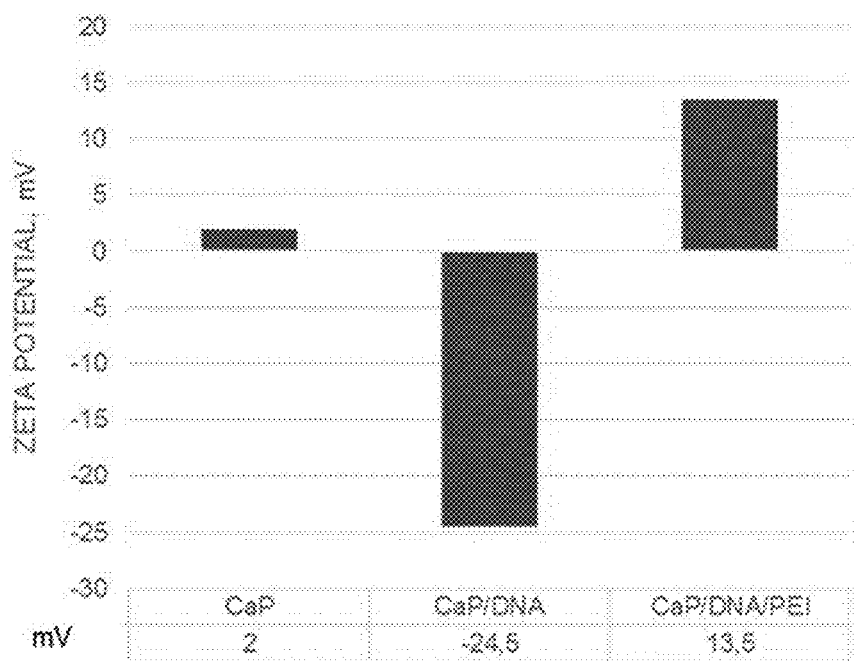
FIG. 4 illustrates a bar graph showing the zeta potential of particles of calcium phosphate without any nucleic acid loaded (CaP), calcium phosphate with loaded-DNA (CaP/DNA) and calcium phosphate/nucleic acid particles capped with PEI polycation (CaP/DNA/PEI) in accordance with one or more embodiments shown and described herein.
Figure 5:
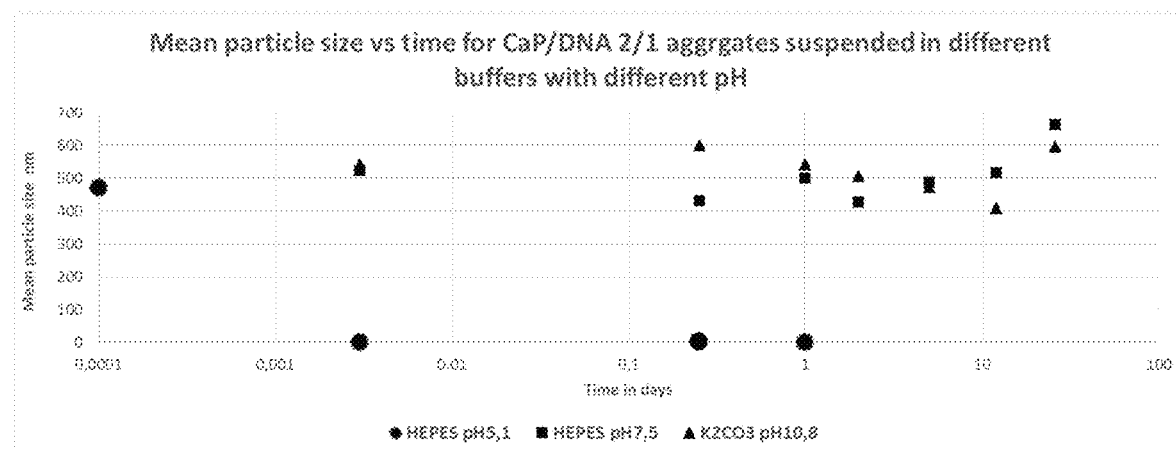
FIG. 5 illustrates a graph showing the size of nucleic acid carrier particles CaP/DNA [2:1] made of nucleic acid and CaP prepared according to the process described in Example 1, at acidic, neutral and basic pH.

Another aspect of the present technology relates to a method for producing hybrid nanoparticles of calcium phosphate and nucleic acid with a capping agent. In various embodiments, a method for preparing the nanoparticle includes co-precipitating the calcium phosphate with the nucleic acid and capping the CaP/nucleic acid particles with a suitable capping agent. Referring now to FIG. 2 an exemplary schematic flow diagram of a process for preparing the nucleic acid-loaded nanoparticle with polycation capping (outer layer) and an idealized view of the resulting hybrid nanoparticles is illustrated. As shown in the figure, the suspension of CaP/nucleic acid particles may be prepared as discussed in reference to FIG. 1 above and the resulting particles may be further capped using suitable capping agent. For example, a solution of the capping agent (or its salt) may be slowly added to the CaP/DNA particles suspension. The suspension may be mixed and further diluted using a suitable solvent, such as water. In various embodiments, the method includes adding a nucleic acid to either a calcium salt solution or a phosphoric acid salt solution, adjusting the pH of either the salt solutions or the mixed solution to a suitable value, mixing the calcium salt solution with said phosphoric acid salt solution to form calcium phosphate-nucleic acid nanoparticles, and adding a capping agent solution to the nanoparticles to demonstrate a hybrid CaP/nucleic acid/capping agent nanoparticle suspension. In various embodiments, the capping method enables the nucleic acid to be at least partially encapsulated in the calcium phosphate nanoparticles and/or coated on to the surface of the nanoparticles because of the binding with the capping agent.

Suitable calcium salts and phosphoric acid salts for the preparation of calcium phosphate are known in the art and may be used in the methods of the present technology. Exemplary calcium salts include, without limitation, calcium chloride, calcium nitrate, calcium acetate and calcium lactate. Exemplary phosphoric acid salts include, without limitation, trisodium phosphate, tripotassium phosphate, potassium hydrogen phosphate, sodium hydrogen phosphate, ammonium phosphate, and ammonium hydrogen phosphate.

Figure 8:
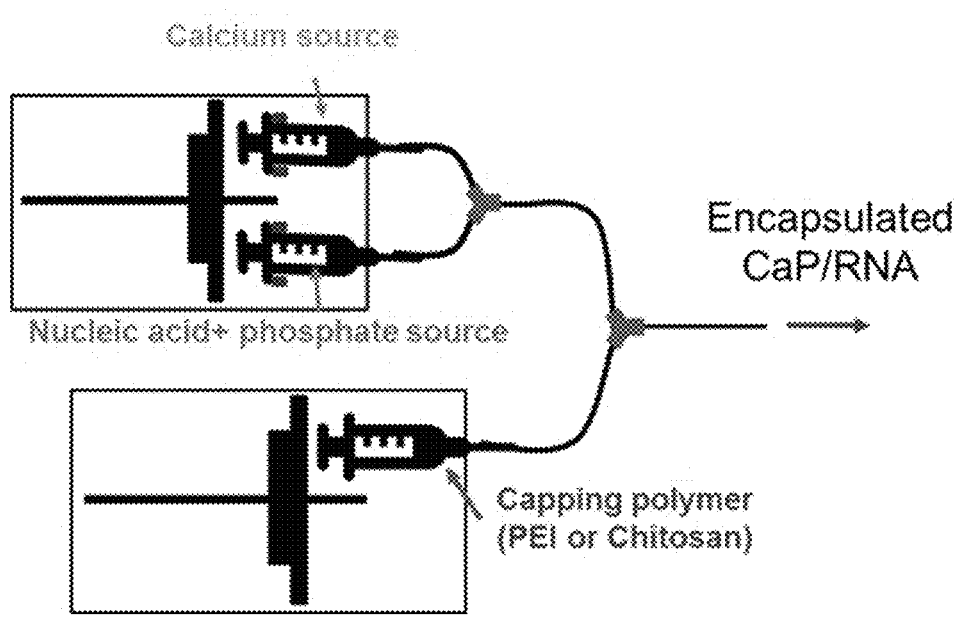
FIG. 8 illustrates a schematic diagram showing the tube flow reactor setup used to prepare the suspension in continuous mode (flow) according to Example 4.
Figure 9:
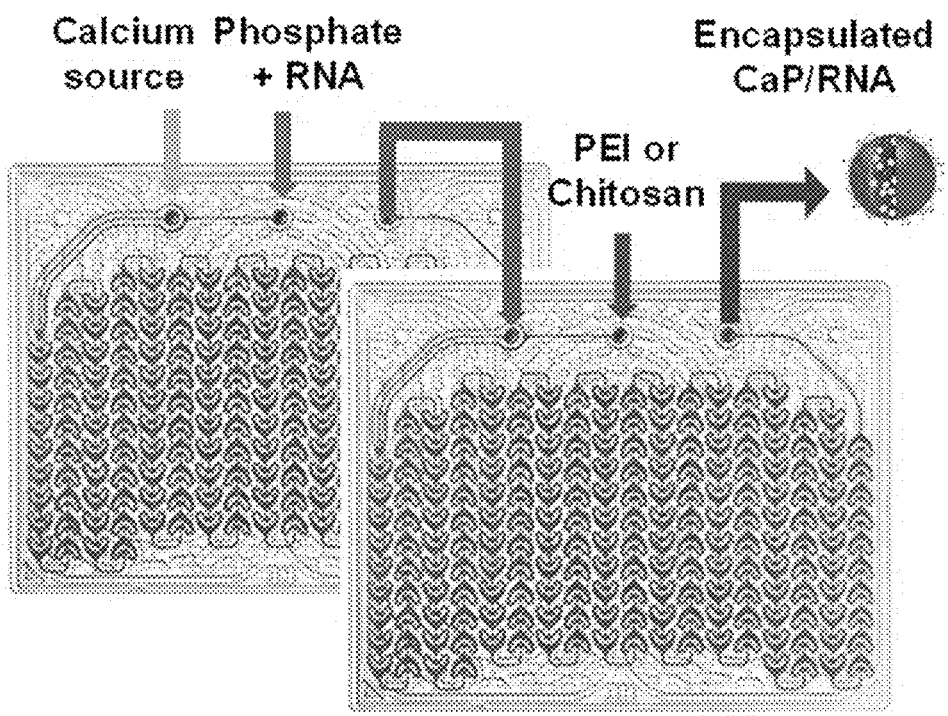
FIG. 9 illustrates a schematic diagram showing a putative AFR reactor setup used to prepare the suspension in continuous mode in accordance with one or more embodiments shown and described herein.

Based on the fast kinetics of formation, the suspension of nucleic acids/calcium phosphate nanoparticles may be advantageously prepared at large scale and low cost using a flow reactor to meet the market demand. Exemplary reactors which may be used for the methods of the present technology include, without limitation a batch reactor, a semi-batch reactor, a continuous flow reactor, an advanced flow reactor, a fluidized bed reactor and a combination thereof. Examples of suitable reactors such as the flow reactor and the advanced flow reactor are depicted in FIGS. 8 and 9, respectively.

In yet another aspect, provided herein is a method for preparing a suspension of hybrid nanoparticles in a continuous flow reactor. The method includes adding a nucleic acid to one of a calcium salt solution or a phosphoric acid salt solution; flowing the calcium salt solution into a first inlet of a flow reactor; flowing the phosphoric acid salt solution into a second inlet of the flow reactor so as to mix the phosphoric acid salt solution stream with the calcium salt solution stream and produce a calcium phosphate-nucleic acid hybrid nanoparticle stream flowing from said reactor; and collecting and processing the suspension comprising calcium phosphate-nucleic acid nanoparticles from the reactor. In certain aspects, the method may further include flowing a capping polymer solution into a third inlet of the flow reactor so as to mix the capping polymer stream with the calcium phosphate stream to produce a polymer capped, nucleic acid encapsulated calcium phosphate stream flowing from said reactor, and collecting and processing the polymer capped, nucleic acid encapsulated calcium phosphate from the reactor.

The binding of nucleic acid on the surface or the capping agent on the surface of the nanoparticles may be studied using the change in zeta-potential of the nanoparticle surface. A change in zeta-potential is indicative of the ligand binding to the surface or surface coating. The zeta-potential is a measure of surface charge on the nanoparticles and may have an impact on both the stability and aggregation of particles in the suspensions. In various embodiments, the nanoparticles are configured in such a way that they have a low zeta potential material at a pH level effective for the nucleic acid incorporation inside the CaP matrix. For the particles having a capping agent, the nanoparticles show a high zeta potential for coating on the surface of the nanoparticle. For example, the CaP/nucleic acid particles may exhibit a negative charge CaP/nucleic acid/capping agents may exhibit a positive charge. In various embodiments, the nanoparticles have a zeta potential of from about −50 to about 50 millivolts (mV), including, from about −50 mV to about 0 mV, −40 mV to about 0 mV, from about −30 mV to about 0 mV, from about −20 mV to about 0 mV, from about −10 mV to about 0 mV, from about 0 mV to about 10 mV, 0 mV to about 20 mV, from about 0 mV to about 30 mV, from about 0 mV to about 40 mV, from about 0 mV to about 50 mV, from about −10 mV to about 10 mV, −15 mV to about 15 mV, from about −20 mV to about 20 mV, from about −25 mV to about 25 mV, from about −30 mV to about 30 mV, or any range including and/or in-between any two of these values.

The nanoparticles formed by the methods of the present technology are suspended in a liquid medium, such as water, alcohol, hydrocarbon, and oil. The nanoparticles may have an average or mean particle size ranging from about 30 nm to about 250 nm, including, from about 40 nm to about 200 nm, from about 50 nm to about 150 nm, from about 60 nm to about 100 nm, from about 70 nm to about 80 nm, or any range including and/or in-between any two of these values.

The nanoparticle compositions and suspensions described herein may be delivered to various types of cells. Any type of cell which is susceptible to delivery of nucleic acids may be used as the target for transformation according to the present technology. Examples include, without limitation insect cells, animal cells and embryos, fungi, fish, yeast, and plant cells. The stable aqueous suspension may be used as part of phytosanitary compositions for controlling pest. For example, the stable suspensions may be used to protect crop against insects, in which case the nucleic acid is insecticidal double stranded RNA. The compositions and suspensions may be used in the prevention and/or control of pest infestation of plants, using interfering ribonucleic acid (RNA) molecules. Compositions and combinations containing the interfering RNA molecules of the technology for use in topical applications, for example in the form of insecticides.

Aspects of the present technology relate to a method of protecting a crop against an insect, the method comprising administering the compositions or suspensions including the nanoparticles described herein to the crop. In various embodiments, the method includes protecting a crop against hemiptera, coleoptera, siphonaptera, dichyoptera, lepidoptera, orthoptera and diptera. The composition may be administered to the crop using various methods known in the art, such as by spraying, drip-feeding, or irrigation. In such methods, the nucleic acid in the composition may include insecticidal double stranded ribonucleic acid.

Another aspect of the present technology relates to methods for down-regulating expression of a target gene in an insect pest species in order to prevent and/or control pest infestation, comprising contacting said pest species with an effective amount the compositions or suspensions of the hybrid nanoparticles described herein comprising at least one interfering ribonucleic acid (RNA). Suitable interfering RNA's are known in the art, for example, as described in PCT Publication No. WO2012143542A1, incorporated herein by reference in its entirety. In certain embodiments, the present technology relates to methods of using the RNAi containing nanoparticle compositions to control pest involved simple topical applications of naked-RNA devoid of any protection on the plant surfaces, e.g. the leaf surfaces.

Another aspect of the present technology relates to a glass container which includes the compositions and aqueous suspensions described herein. Any glass container suitable for holding liquid materials and is inert to or does not react with the compositions and suspensions, may be used. Exemplary glass containers include glass bottles, glass vials, glass barrels, glass capsules, glass jars, glass cans, glass balls, and the like.

The compositions and suspensions of the present technology advantageously provide calcium phosphate/nucleic acid nanoparticles wherein the inorganic material surrounding the nucleic acids is calcium phosphate, which is stable at neutral and basic pH and dissolves quickly at acidic pH. Therefore, the particles are stable in the environment and in basic medium present in the insect gut, protecting to some degree the nucleic acids, but will dissolve quickly at endosomal pH releasing the nucleic acid inside the cell of the target insects. The submicron particles carrying the nucleic acid such an insecticidal RNA are readily absorbed by the cell of the digestive channel of the target pest. The amount of nucleic acid loaded in the hybrid calcium phosphate/nucleic acid nanoparticles, also called payload, may be higher than 30 wt. % without any polycation added which is much higher than that provided by the methods known in the art. Consequently, the amount of inorganic carrier to be sprayed on the field may be minimized, as a lower amount of the carrier will be able to deliver the effective amount of the insecticidal dose. The co-precipitation approach used in the technology enables much higher nucleic acid loading than simple surface adsorption as described by in the prior art. Indeed, the amount of nucleic adsorbed on a carrier surface remains limited, e.g. less than 1 wt. %, even when submicron size particles are used. In case of co-precipitation process used in the present technology, the nucleic acids are trapped in a large quantity inside the composite structure and not only at the surface of the carrier. The inventors found that more than 90% of the nucleic acids are trapped during the particles formation which provides a high encapsulation yield and avoids wasting the expensive nucleic acids. When a polycation, e.g. PEI, is applied onto the surface of the nucleic acid/calcium phosphate particles, the yield reaches almost 100% since the polycation is able to capture the nucleic that were not bound during the co-precipitation process. The calcium phosphate material forming the carrier is completely biocompatible, biodegradable, non-toxic, and non-immunogenic and prepared from safe and cheap reagents such as calcium salts and phosphate salts, which results in ease and low cost of production. When used for crop protection, beyond its pest control action, the nucleic acid/calcium phosphate particles may be regarded as potential fertilizers since they are a source of phosphorous. The availability of the phosphorous is facilitated by the submicron size of the particle which promotes fast dissolution in acidic environments. The method of the technology enables the preparation of stable suspension, i.e., exempt of aggregation, to be used in phytosanitary compositions. The stable suspension can contain at least 20 μg/ml of double stranded nucleic acid, e.g. RNA, which is typically what is required for crop protection using an RNA interference. The loaded particles and their suspensions are stable for weeks and may be sprayed as is or incorporated within an emulsion to be sprayed on the plants.

It will be apparent to those skilled in the art that various modifications and variations may be made without departing from the spirit or scope of the claimed subject matter. Accordingly, the claimed subject matter is not to be restricted except in light of the attached claims and their equivalents.

Examples

Various embodiments will be further clarified by the following examples, which are in no way intended to limit this disclosure thereto.

Example 1: Preparation of Stable Nucleic Acid/CaP Nanoparticle Suspension

In a glass vial was added 718.6 μl pure $H_2O$, 500 μl sol HEPES (50 mM, pH 7.5) containing 7.5 mM $Na_3PO_4$ and 31.4 μl of 10 mg/ml sheared salmon sperm ds-DNA. Then a second mixture containing 1150 μl of 10 mM Tris HCl at pH 7.5 and 100 μl of 62.5 mM $CaCl_2$) in UP water was added dropwise under intense stirring. The total volume was 2500 μl. The particle suspension was immediately diluted by adding 2,500 μl of the prepared particle suspension into 10,000 μl UP water. The final volume was 12,500 μl. The solution contains theoretically 628 μg of calcium phosphate and 314 μg of DNA based on the feed. The theoretical nucleic acid loading was therefore about 33 wt. %. The concentration of nucleic acid in the final suspension was about 24 μg/ml and the theoretical concentration of calcium phosphate was 48 μg/ml. The resulting stable suspension is made of particles with average hydrodynamic diameter of 49 nm and average zeta potential of −11 mV.

Characterization of the particle size of an aqueous suspension was provided using Malvern Zetasizer Nano Analyzer which determines the hydrodynamic diameter of the particles by dynamic light scattering (DLS) techniques. FIG. 3 shows a DLS graph showing the size of CaP/DNA particle prepared by co-precipitation without any polycation, the size of the polyplex resulting from the complexation of the DNA and the PEI polycation without any CaP, and finally the size of the particle prepared by co-precipitation but with PEI capping. The graph clearly show that the CaP/DNA/PEI particle has the biggest hydrodynamic diameter and is significantly greater than that of the simple DNA/PEI polyplex. The graph also shows that narrow particle size distributions may be achieved. FIG. 4 is a bar graph showing the zeta potential of particles of calcium phosphate without any nucleic acid loaded (CaP), calcium phosphate with loaded-DNA (CaP/DNA) and calcium phosphate/nucleic acid particles capped with PEI polycation (CaP/DNA/PEI). The particles exhibit a neutral, negative and positive charge, respectively.

The suspension exhibits a limited stability over time. A graph showing the size of nucleic acid carrier particles CaP/DNA [2:1] made of nucleic acid and CaP at acidic, neutral and basic pH is illustrated in FIG. 5, and the change in particle size over time under various pH conditions is summarized in Table 2 below. The data shows the quick dissolution of the nucleic acid carrier at acidic pH and absence of dissolution at neutral and basic pH.

TABLE 2

| | Mean Particle Size (nm) | | |
|---|---|---|---|
| Time (days) | HEPES pH 5.1 | HEPES pH 7.5 | $K_2CO_3$ pH 10.8 |
| 0 | 471 | 471 | 471 |
| 0.003 | 0.65 | 524 | 543 |
| 0.25 | 0.7 | 433 | 601 |
| 1 | 0.8 | 501 | 543 |
| 2 | — | 428 | 507 |
| 5 | — | 489 | 474 |
| 12 | — | 517 | 408 |
| 26 | — | 664 | 597 |

As a comparative example, the same protocol was repeated except that the suspension was not diluted after particles formation. The resulting suspension contains 125 μg/ml of nucleic acid and 215 μg/ml calcium phosphate. It was observed that the obtained stable suspension is made of particles with average hydrodynamic diameter of 220 nm and average zeta potential of −26 mV. Despite a high zeta potential, the suspension shows a rapid increase of the particle size exceeding 10 μm as shown on FIG. 7.

Example 2: Scaled-Up Preparation of Stable Nucleic Acid/CaP Nanoparticle Suspension Example 1 was repeated except that all quantities were multiplied by 5 to show that the formation of the nanoparticles may be scaled up without significant impact on the obtained particle size or surface charge. A stable suspension with particle having the same size and same surface charge was obtained.

Example 3: Preparation of Stable PEI-Capped Nucleic Acid/CaP Nanoparticle Suspension In a glass vial was added 718.6 µl pure $H_2O$, 500 µl sol HEPES (50 mM, pH 7.5) containing 7.5 mM trisodium phosphate $Na_3PO_4$ and 31.4 µl of 10 mg/ml sheared salmon sperm ds-DNA as surrogate for ds-RNA. Then a second mixture containing 1150 µl of 10 mM Tris HCl at pH 7.5 and 100 µl of 62.5 mM $CaCl_2$ in UP water was added dropwise in the former solution under intense stirring. Then, 628 µl of 1 µg/µl linear PEI hydrochloride (prepared from PEI Mw 25,000, Catalog #23966-1) from Polysciences, Inc. (Warrington, Pa., USA) and converted to its chloride salt according to the supplier protocol) in water at pH 7 was added dropwise into the CaP/DNA particles suspension. The total volume obtained was 3,128 µl.

The particle suspension was immediately diluted by dropping 3,128 µl of the prepared particles suspension into 12,512 µl UP water under stirring. The final volume was 15,640 µl. The solution contains 628 µg of calcium phosphate and 314 µg of DNA and 628 µg of PEI. The particle composition was observed to have a CaP/DNA/PEI ratio of 2:1:2. The theoretical nucleic acid loading in the particle was therefore 20 wt. %. The concentration of nucleic acid in the final suspension was about 20 µg/ml, the concentration of PEI was about 40 µg/ml and the theoretical concentration of calcium phosphate was about 40 g/ml. It was observed that the obtained stable suspension is made of particle with hydrodynamic diameter of about 155 nm and a zeta potential of +22 mV. The suspension exhibits very high stability over time and do not show any sign of particles growth after at least 20 days.

As a comparative example, the same protocol was repeated except that the suspension was not diluted right after particles formation. The resulting suspension contains 100 µg/ml of nucleic acid, 200 µg/ml calcium phosphate and 200 µg/ml PEI.

Figure 6:
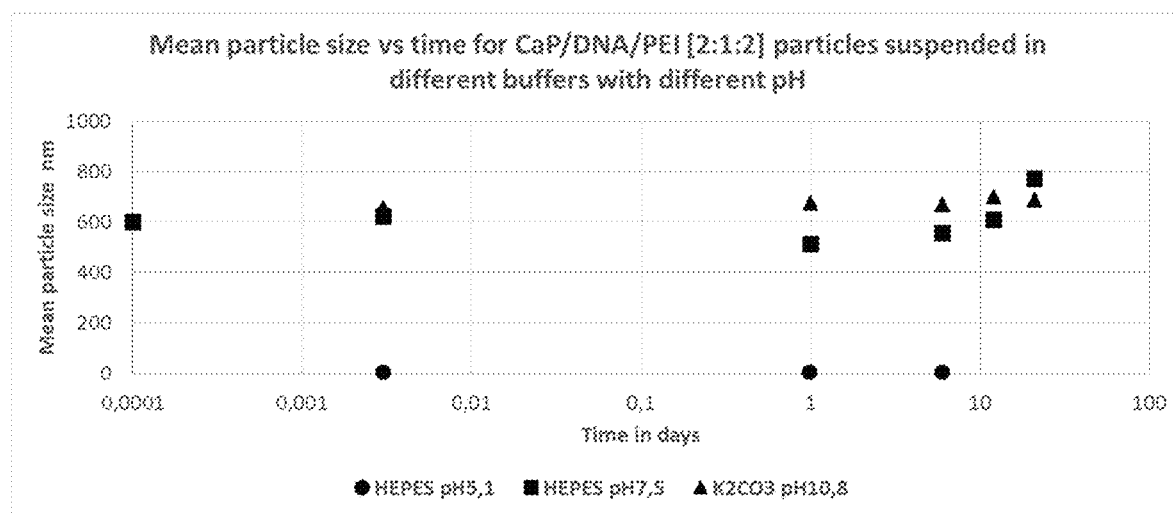
FIG. 6 illustrates a graph showing the size of nucleic acid carrier particles CaP/DNA/PEI [2:1:2] made of nucleic acid, CaP and PEI outer layer prepared according to the process described in Example 3, at acidic, neutral and basic pH.

A graph showing the size of nucleic acid carrier particles CaP/DNA/PEI [2:1:2] made of nucleic acid, CaP and PEI outer layer at acidic, neutral and basic pH is illustrated in FIG. 6, and the change in particle size over time under various pH conditions is summarized in Table 3 below.

TABLE 3

| | Mean Particle Size (nm) | | |
|---|---|---|---|
| Time (days) | HEPES pH 5.1 | HEPES pH 5.1 | HEPES pH 5.1 |
| 0 | 600 | 600 | 600 |
| 0.003 | 0.77 | 624 | 656 |
| 1 | 0.82 | 512 | 677 |
| 6 | 0.8 | 557 | 670 |
| 12 | — | 612 | 700 |
| 21 | — | 773 | 690 |

Figure 7:
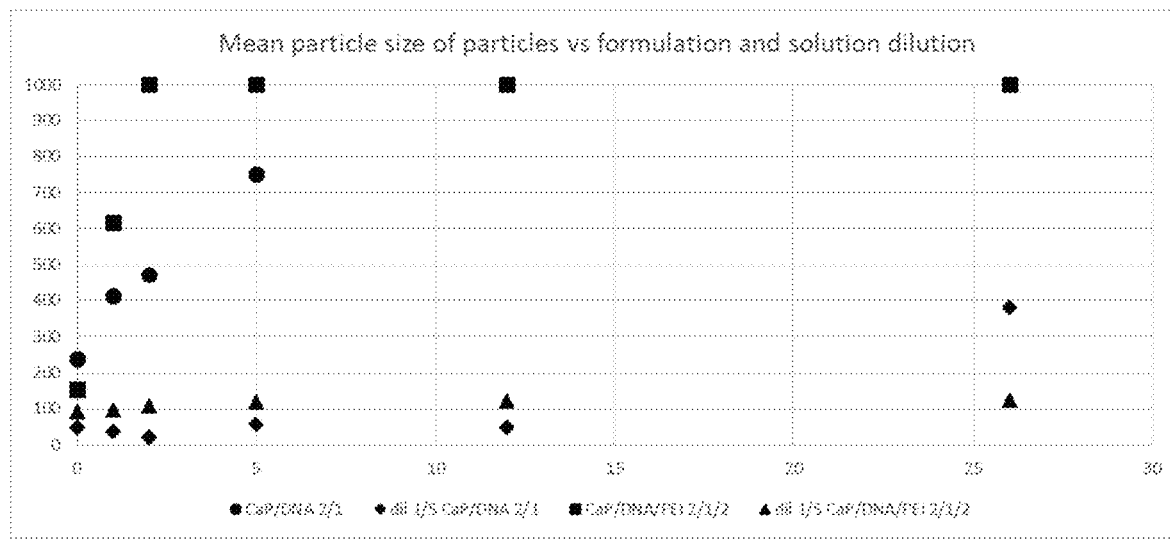
FIG. 7 illustrates a graph showing the evolution of particle size diluted and undiluted CaP/DNA [2:1] and CaP/DNA/PEI [2:1:2].

The suspension shows a rapid increase of the particle size exceeding 10 µm as shown on FIG. 7. It was observed that the obtained stable suspension is made of particle with hydrodynamic diameter of 164 nm and zeta potential of +22 mV. Despite a high zeta potential, the suspension shows a rapid increase of the particle size exceeding 10 µm after 5 days storage at RT as shown on FIG. 7. The particle size, zeta potential and suspension stability for undiluted and diluted compositions prepared according to Examples 1 and 3 are summarized in Table 4 below.

TABLE 4

| | CaP/DNA [2:1] From example 1 | | CaP/DNA/PEI [2:1:2] From example 3 | |
|---|---|---|---|---|
| | Undiluted | Diluted | Undiluted | Diluted |
| Total solids (µg/ml) | 377 | 75 | 501 | 119 |
| Mean particle size (nm) | 220 | 49 | 164 | 155 |
| Zeta potential (mV) | −26 | −11 | +22 | +22 |
| Suspension stability | flocculate | Stable | flocculate | Stable |

Example 4: Preparation of Stable PEI-Capped Nucleic Acid/Calcium Phosphate Nanoparticle Suspension in a Continuous Mode The reactor setup for the preparation of stable PEI-capped nucleic acid/calcium phosphate nanoparticle suspension in a continuous mode was used as shown in the scheme in FIG. 8. Briefly, a small scale tube flow reactor was prepared using a two-Syringe Infusion Pump connected to a Y-Connector made of PEEK via two PFA 1/16" OD Tube. The exit of the Y-Connector was connected to a PFA 1/16" OD tubing to collect the suspension. A third syringe was placed downstream and connected via a second Y-Connector. The first syringe (total volume capacity=1.5 ml) was filled with a solution containing 718.6 µl pure $H_2O$, 500 µl sol HEPES (50 mM, pH 7.5) containing 7.5 mM $Na_3PO_4$ and 31.4 µl of 10 mg/ml sheared salmon sperm ds-DNA. The second syringe was filled with 1150 µl 10 mM Tris HCl at pH 7.5 and 100 µl 62.5 mM $CaCl_2$ in UP $H_2O$. The third syringe was filled with 628 µl of 1 µg/µl linear PEI hydrochloride of Mw 25,000. The reagents were delivered at a suitable rate to yield 150-200 nm particle size nanoparticles.

Alternatively, other types of micro passage reactors, such as the Advanced Flow Reactor (AFR) of Corning Inc., can also be used to prepare stable PEI-capped nucleic acid/calcium phosphate nanoparticle suspension in a continuous mode, as shown in FIG. 9.

Example 5: Nucleic Acid Capture Measurement

The efficiency of nucleic acid capture during the co-precipitation process was estimated by measuring the optical density of the supernatant at 260 nm after centrifugation of the suspension at 13000 rpm/4° C. for 60 min. 100 µl of 880 µg/ml $CaCl_2$ was added in to each test sample to destabilize the suspension (it was verified that such addition of $CaCl_2$ does not induce any precipitation of the naked nucleic acids). The blank was made with DNA only without any CaP. A calibration curve was prepared using various DNA concentrations ranging from 0 to 125 µg/ml. The wt. % of nucleic loaded in the hybrid nanoparticle, i.e., payload, was indirectly estimated by using the theoretical amount of formed CaP calculated from the concentration of the salt precursors, assuming the precursors led to $Ca_5(PO_4)_3(OH)$, and the amount of captured nucleic acids determined from the OD value. In the case of the PEI capped particles the amount of PEI was added to the amount of CaP and nucleic acid to calculate the total mass of carrier. The concentration of nucleic acid (DNA) in the samples before and after co-precipitation is summarized in Table 5 below. The results show that most of the nucleic acids was captured during the precipitation of the calcium phosphate.

TABLE 5

| Sample | Initial dsDNA concentration before centrifugation (µg/ml) | dsDNA concentration in supernatant after centrifugation (µg/ml) | % of initial dsDNA captured by co-precipitation | Nucleic acid payload vs total solid (%) |
|---|---|---|---|---|
| DNA only (blank) | 120 | 120 | 0 | — |
| CaP/DNA [2:1] | 120.8 | 1.6 | 98.6 | 33.8 |
| CaP/DNA/PEI [2:1:2] | 92.3 | 6.3 | 93.2 | 18.6 |

The mass loading ratio (payload) was determined for the CaP/dsDNA/PEI using different mass ratio such as 0:1:0, 2:1:0, 2:1:2.

Example 6: Measurement of Cell Uptake of Hybrid CaP/DNA/PEI Nanoparticle

Figure 10A:
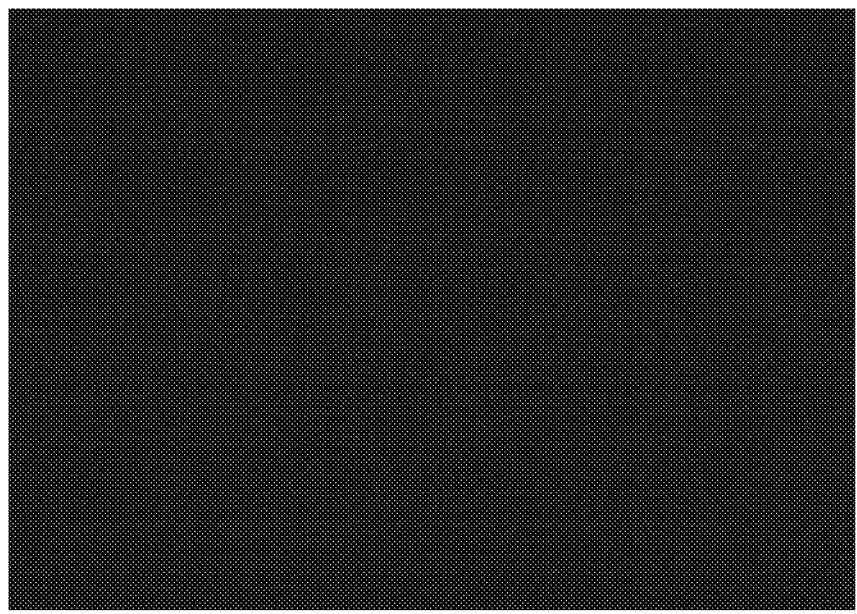
FIGS. 10A and 10B shows the fluorescent images of the negative control and the cells that were transfected by the GFP plasmid, respectively, in accordance with one or more embodiments shown and described herein.
Figure 10B:
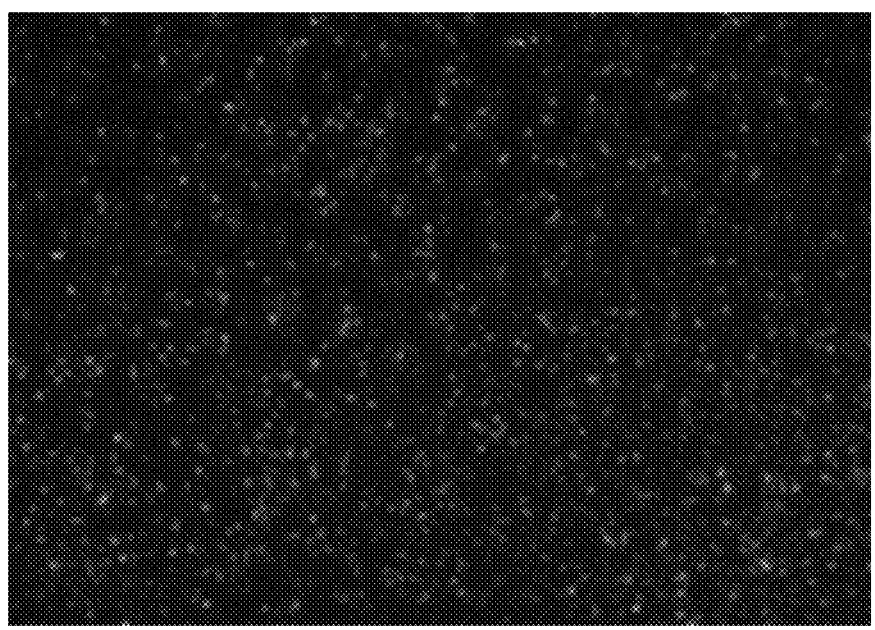

In order to show that the nucleic acid loaded in the novel hybrid CaP/DNA/PEI nanoparticle may be internalized by cell and that the nucleic acid was still functional, CaP/DNA/PEI [2:1:2] particles were prepared according to example 3, but 10 wt. % of the salmon sperm DNA, i.e. 31.4 µg, was replaced by the same amount of GFP plasmid, coding for the green fluorescent protein (GFP). 500K cells were seeded into each well of a 6 W Cell bind plate in 4 ml medium (RPMI+10% FBS+PS+Glu) and let to attach and grow for one day. Then the culture medium was exchanged and a volume of suspension corresponding to 5.1 µg total DNA, and thus 0.51 µg plasmid, was added to the well. One day after addition of the particles suspension to the cell monolayer, the cells were harvested and expression of green fluorescent protein (GFP) was determined by flow cytometry. The fluorescence of the cells that were transfected by the GFP plasmid using the nanoparticle carrier and that of the negative control having the HEK 293 T cell without any transfection agent added, are depicted in FIGS. 10a and 10b, respectively. The results show that more than 65% of the cells expressed the GFP, which demonstrates that the nucleic acid-loaded hybrid particles of the technology was internalized and transfection occurred, while the negative control showed no fluorescence.

Example 7: Preparation of Stable PEI-Capped Nucleic Acid/Calcium Phosphate Nanoparticle Suspension The process described in example 3 was repeated except that the amount of DNA was adapted to achieve Cap/DNA/PEI mass ratio of [2:2:2]. It was observed that the stable suspension obtained was made of particle with hydrodynamic diameter of about 197 nm. The suspension exhibits good stability over time and does not show any sign of flocculation.

Example 8: Preparation of Stable PEI-Capped Nucleic Acid/Calcium Phosphate Nanoparticle Suspension at Varying DNA Concentration The process described in example 3 was repeated except that the Cap/DNA/PEI mass ratio was varied to 2:1:2, 2:2:2, 2:3:2, 2:4:2, 2:5:2, 2:7.5:2, 2:10:2 and 2:20:2.

Figure 11:
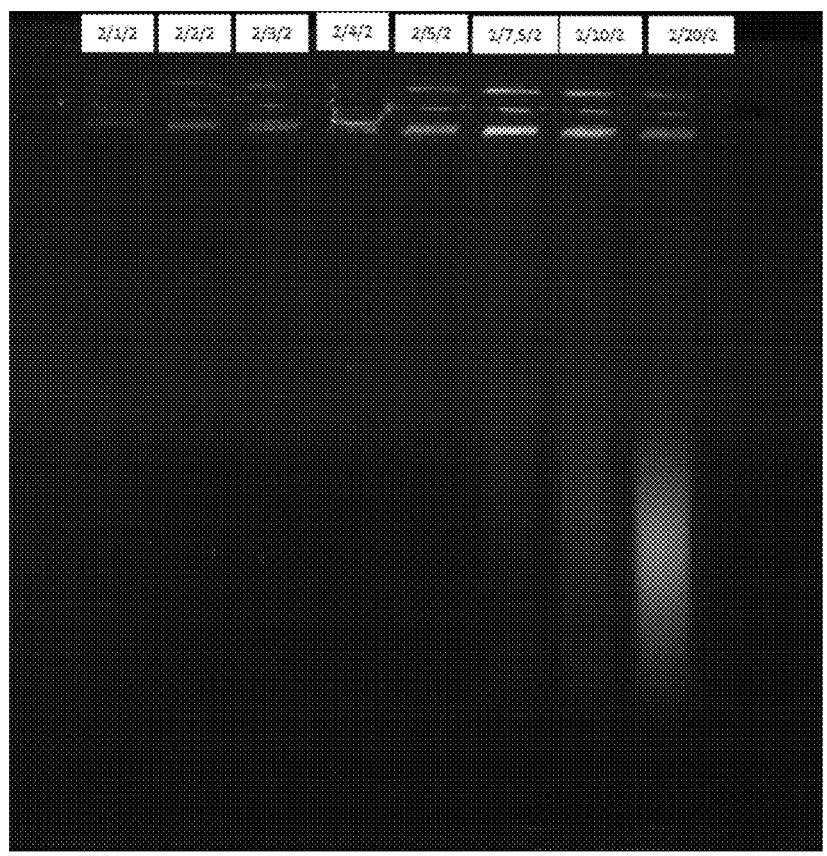
FIG. 11 shows the electrophoretic mobility of DNA patterns in various nanoparticle samples in accordance with one or more embodiments shown and described herein.

The resulting mixtures were subjected to gel electrophoresis using a 0.8% agarose gel. As illustrated in FIG. 11, as the amount of nucleic acid increases relative to CaP and PEI, the intensity of the bottom band for free DNA became stronger, indicating that some DNA was unbound. Complete binding of nucleic acid with CaP/PEI was observed to be from 2:1:2 to 2:5:2. Such ratio corresponds to 20 wt. % to 55 wt. % DNA loading. At these ratios all nucleic acid are associated to CaP/PEI leaving no free DNA to migrate down the gel.

Example 9: Preparation of Stable dsRNA/Calcium Phosphate [2:1] Nanoparticle Suspension The process of example 1 was repeated except that dsRNA was used instead of dsDNA. Buffers were prepared from nuclease free water and autoclaved prior use. Manipulations were performed according to good lab practices to prevent contamination by nucleases. To demonstrate that dsRNA having various size may be incorporated into the particle, annealed double-stranded RNA fragments having 21 to 500 base pairs were used. The theoretical dsRNA loading of the hybrid particles prepared is about 33 wt. %. The concentration of nucleic acid in the final suspension is about 24 µg/ml and the theoretical concentration of calcium phosphate is 48 µg/ml. It was observed that the obtained stable suspension is made of particle with hydrodynamic diameter of 120 nm and zeta potential of −18 mV.

Figure 12:
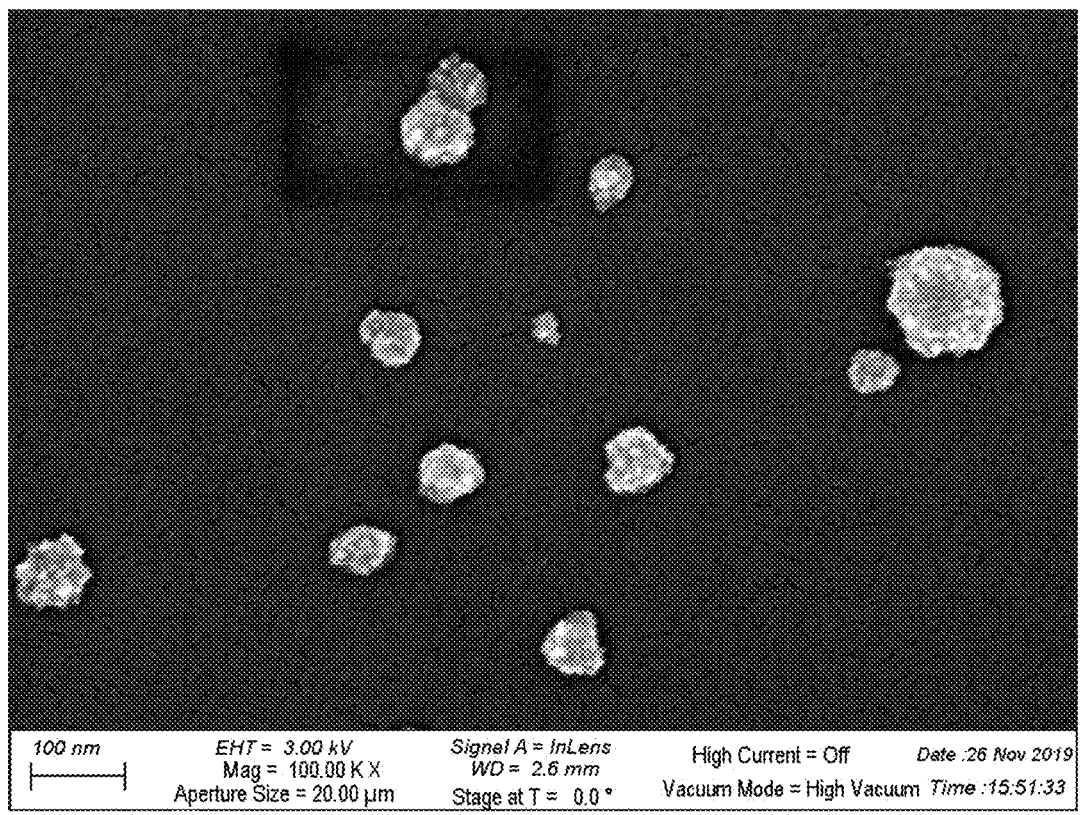
FIG. 12 shows the SEM micrograph showing the morphology of nanoparticles prepared from a dsDNA/calcium phosphate/PEI [2:4:0] (in the dry state) prepared according to the process described in Example 13.

Example 10 Preparation of Stable dsDNA/Calcium Phosphate Nanoparticle Suspension at [2:4] Weight Ratio Example 1 was repeated except that the weight ratio CaP to DNA was 2:4. The morphology of nanoparticles prepared from a dsDNA/calcium phosphate/PEI [2:4:0] (in the dry state) is depicted in the SEM micrograph shown in FIG. 12.

Example 11 Preparation of Stable dsDNA/Calcium Phosphate/Polycation [2:1:2] Nanoparticle Suspension Using Poly (N, N-Dimethylamino Ethyl Methacrylate), PDMAEMA, Instead of PEI The process of example 3 was repeated except that PDMAEMA, Mn 33.000, available from Polymer Source Inc. was used instead of linear PEI. The pH of the 1 µg/µl PDMAEMA solution was adjusted to 7.2 using hydrochloric acid before performing the co-precipitation process. The particles obtained exhibit a hydrodynamic diameter of 195 nm as measured by DLS and a zeta potential of +21 mV.

Figure 13A:
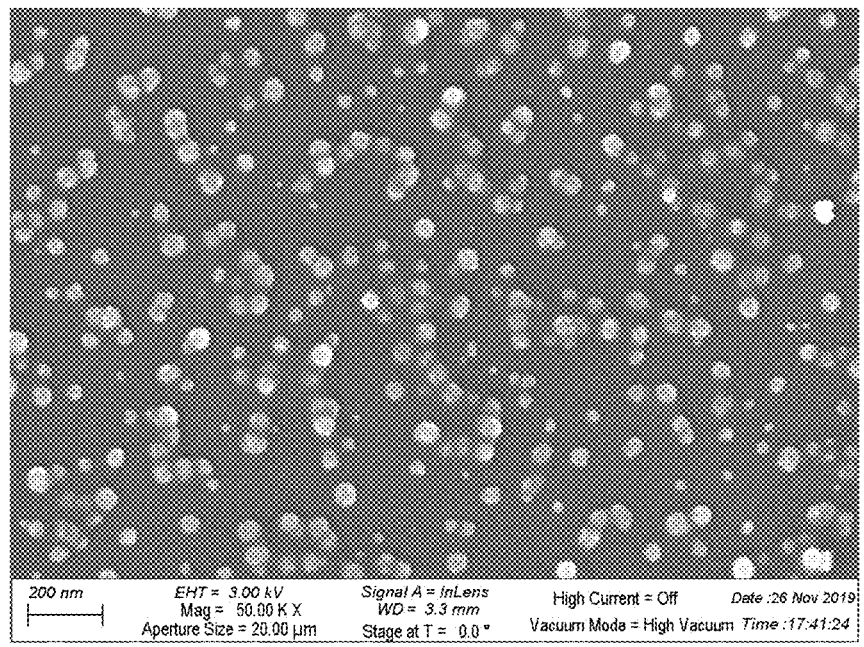
FIGS. 13A and 13B show SEM micrographs at two magnifications showing the morphology and size of nanoparticles prepared from a dsDNA/calcium phosphate/PEI [2:1:2] (in the dry state).
Figure 13B:
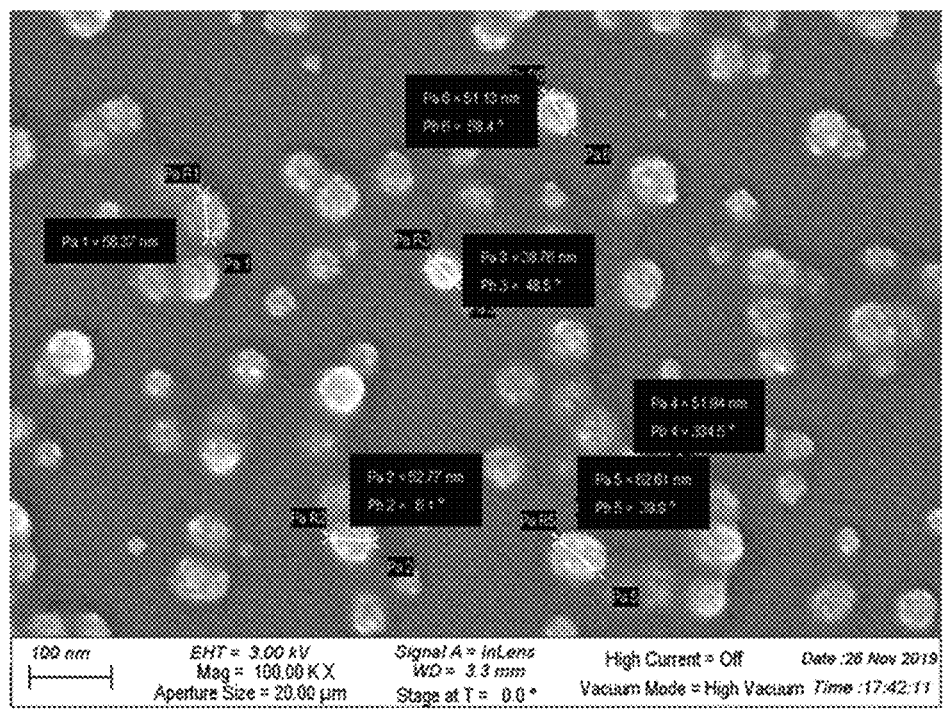

Example 12 Preparation of Stable dsDNA/Calcium Phosphate/Polycation [2:1:2] Nanoparticle Suspension Using Branched PEI The process of example 3 was repeated except that branched PEI, average Mw~25,000 by LS, average Mn~10, 000 by GPC, Sigma Aldrich, was used instead of linear PEI. The particle exhibits a hydrodynamic diameter of 156 nm and a zeta potential of +28 mV. The SEM micrographs at two magnifications showing the morphology and size of nanoparticles prepared from a dsDNA/calcium phosphate/ PEI [2:1:2] (in the dry state) are depicted in FIGS. 13A and 13B. The average size of the particles is 52 nm, and they have homogenous size distribution.

Example 13 Preparation of Stable dsRNA/Calcium Phosphate/PEI [2:1:2] Nanoparticle Suspension The process of example 3 was repeated except that dsRNA was used instead of dsDNA similar to what is described in example 9. For the diluted solution, the theoretical nucleic acid loading in the particle is therefore 20 wt. % for the [2:1:2] ratio. The concentration of dsRNA in the final suspension is about 20 μg/ml, the concentration of PEI is about 40 μg/ml and the theoretical concentration of calcium phosphate is about 40 g/ml. It was observed that the obtained stable suspension is made of particle with hydrodynamic diameter of about 188 nm and a zeta potential of +24 mV.

Figure 14:
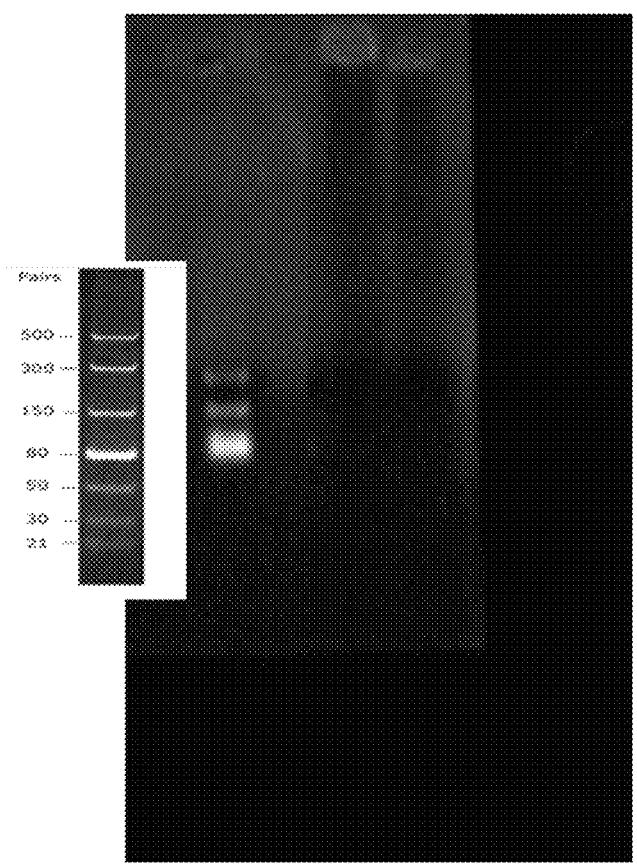
FIG. 14 is an image showing gel retardation experiment (0.8% agarose) performed on dsRNA/calcium phosphate/PEI [2:1:2] nanoparticle suspension at two concentration prepared according to the process described in Example 10.

The suspension was also prepared without dilution as described in example 10 (noticed "cone" for concentrated). To demonstrate that all dsRNA is bound, the obtained suspension was subjected to gel electrophoresis using a 0.8% agarose gel. As illustrated in FIG. 14 complete binding of dsRNA with CaP/PEI was demonstrated for such 2:1:2 ratio. At these ratios all nucleic acids are associated to CaP/PEI leaving no free DNA to migrate down the gel. Such ratio corresponds to 20 wt. % dsRNA loading.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

All disclosed ranges are to be understood to encompass and provide support for claims that recite any and all subranges or any and all individual values subsumed by each range. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth). Any listed range may be easily recognized as sufficiently describing and enabling the same range being broken down into at least equal halves, thirds, quarters, fifths, tenths, etc. As a non-limiting example, each range discussed herein may be readily broken down into a lower third, middle third and upper third, etc. As will also be understood by one skilled in the art all language such as "up to," "at least," "greater than," "less than," and the like, include the number recited and refer to ranges which may be subsequently broken down into subranges as discussed above. Finally, as will be understood by one skilled in the art, a range includes each individual member. Thus, for example, a group having 1-3 layers refers to groups having 1, 2, or 3 layers. Similarly, a group having 1-5 layers refers to groups having 1, 2, 3, 4, or 5 layers, and so forth.

The drawings shall be interpreted as illustrating one or more embodiments that are drawn to scale and/or one or more embodiments that are not drawn to scale. This means the drawings may be interpreted, for example, as showing: (a) everything drawn to scale, (b) nothing drawn to scale, or (c) one or more features drawn to scale and one or more features not drawn to scale. Accordingly, the drawings can serve to provide support to recite the sizes, proportions, and/or other dimensions of any of the illustrated features either alone or relative to each other. Furthermore, all such sizes, proportions, and/or other dimensions are to be understood as being variable from 0-100% in either direction and thus provide support for claims that recite such values or any and all ranges or subranges that may be formed by such values.

The terms recited in the claims should be given their ordinary and customary meaning as determined by reference to relevant entries in widely used general dictionaries and/or relevant technical dictionaries, commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used in a manner that is more expansive than its ordinary and customary meaning, the term should be given its ordinary and customary meaning plus the additional expansive meaning, or (b) if a term has been explicitly defined to have a different meaning by reciting the term followed by the phrase "as used in this document shall mean" or similar language (e.g., "this term means," "this term is defined as," "for the purposes of this disclosure this term shall mean," etc.). References to specific examples, use of "i.e.," use of the word "technology," etc., are not meant to invoke exception (b) or otherwise restrict the scope of the recited claim terms. Other than situations where exception (b) applies, nothing contained in this document should be considered a disclaimer or disavowal of claim scope.

Unless otherwise defined, all terms (including technical and scientific terms) used herein have the same meaning as commonly understood by one of ordinary skill in the art to which this technology belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. While not explicitly defined below, such terms should be interpreted according to their common meaning.

In addition, where features or aspects of the disclosure are described in terms of Markush groups, those skilled in the art will recognize that the disclosure is also thereby described in terms of any individual member or subgroup of members of the Markush group.

Unless the context indicates otherwise, it is specifically intended that the various features of the technology described herein may be used in any combination. Moreover, the disclosure also contemplates that in some embodiments, any feature or combination of features set forth herein may be excluded or omitted. To illustrate, if the specification states that a complex comprises components A, B and C, it is specifically intended that any of A, B or C, or a combination thereof, may be omitted and disclaimed singularly or in any combination.

Unless explicitly indicated otherwise, all specified embodiments, features, and terms intend to include both the recited embodiment, feature, or term and biological equivalents thereof.

All patents, patent applications, provisional applications, and publications referred to or cited herein are incorporated by reference in their entirety, including all figures and tables, to the extent they are not inconsistent with the explicit teachings of this specification.

What is claimed is:

1. A composition comprising nanoparticles, wherein said nanoparticles comprise a nucleic acid at least partially encapsulated within a matrix comprising calcium phosphate, wherein the composition further comprises a capping agent at least partially coating the nanoparticle, wherein the nanoparticles with the capping agent have a peak particle size range of 150 nm to 500 nm, and the capping agent comprises polyethyleneimine, and wherein either the weight ratio of calcium phosphate to nucleic acid in the nanoparticle is from 100:1 to 1:1.5, or the weight ratio of calcium phosphate to nucleic acid to capping agent in the nanoparticle is 2:1:2 to 2:5:2.

2. The composition of claim 1, wherein the nucleic acid comprises ribonucleic acid, deoxyribonucleic acid, or derivatives thereof.

3. The composition of claim 1, further comprising a capping agent permeating the nanoparticle.

4. The composition of claim 1, wherein the ratio of number of positively charged nitrogen atoms of the polycation to the number of phosphorus atoms of the nucleic acid is greater than 1.

5. The composition of claim 1, wherein the nanoparticles are suspended in an aqueous dispersion having a pH of 6 to 11.

6. A stable aqueous suspension comprising the composition of claim 1.

7. The stable aqueous suspension of claim 6, wherein nucleic acid loading is from about 0.1 wt. % to about 50 wt. % with respect to the total mass of the nanoparticles.

8. The stable aqueous suspension of claim 6, wherein:
(i) the concentration of calcium phosphate in the suspension is less than 100 µg/ml; or
(ii) the molar ratio of calcium to phosphorous in the calcium phosphate suspension is from 1.5:1 to 5:1.

9. The stable aqueous suspension of claim 7, further comprising an additive selected from the group consisting of nuclease inhibitors, surfactants, wetting agents, UV absorbers, antioxidant, antifreeze agents, preservatives, coloring agents, insecticides, fungicides, attractants, repellent, and rheology modifiers.

10. A method of protecting a crop against an insect, the method comprising administering the composition of claim 1 to the crop.

11. The method of claim 10, wherein the nucleic acid in the composition comprises insecticidal double stranded ribonucleic acid.

12. The method of claim 10, wherein the method includes protecting a crop against hemiptera, coleoptera, siphonaptera, dichyoptera, lepidoptera, orthoptera and diptera.

13. A method for producing hybrid nanoparticles of claim 1, the method comprising: adding a nucleic acid to one of a calcium salt solution or a phosphoric acid salt solution in a reactor; adjusting the pH of said calcium and phosphoric acid salt solutions to about 6 to about 9; and mixing said calcium salt solution with said phosphoric acid salt solution to form calcium phosphate-nucleic acid hybrid nanoparticles, wherein the nucleic acid is at least partially encapsulated within a matrix comprising the calcium phosphate, and wherein the weight ratio of calcium phosphate to nucleic acid in the nanoparticle is from 100:1 to 1:1.5.

14. The method of claim 13, further comprising adding polyethyleneimine to said mixed solution.

15. The method of claim 13, wherein; (i) the calcium salt is selected from a group consisting of calcium chloride, calcium nitrate, calcium acetate and calcium lactat; or (ii) the phosphoric acid salt is selected from a group consisting of trisodium phosphate, tripotassium phosphate, potassium hydrogen phosphate, sodium hydrogen phosphate, ammonium phosphate, and ammonium hydrogen phosphate.

16. A method for preparing a suspension of hybrid nanoparticles of claim 1 in a continuous flow reactor comprising: adding a nucleic acid to one of a calcium salt solution or a phosphoric acid salt solution; flowing the calcium salt solution into a first inlet of a flow reactor; flowing the phosphoric acid salt solution into a second inlet of the flow reactor so as to mix the phosphoric acid salt solution stream with the calcium salt solution stream and produce a calcium phosphate-nucleic acid hybrid nanoparticle stream flowing from said reactor; collecting and processing the suspension comprising calcium phosphate-nucleic acid hybrid nanoparticles from the reactor, wherein said nanoparticles comprise a nucleic acid at least partially encapsulated within a matrix comprising calcium phosphate, and wherein the weight ratio of calcium phosphate to nucleic acid in the nanoparticle is from 100:1 to 1:1.5.

17. The method of claim 16 further comprising flowing a capping polymer solution into a third inlet of the flow reactor so as to mix the capping polymer stream with the calcium phosphate stream to produce a polymer capped, nucleic acid encapsulated calcium phosphate stream flowing from said reactor.

18. The method of claim 17 further comprising collecting and processing the polymer capped, nucleic acid encapsulated calcium phosphate from the reactor.

19. The method of claim 16, wherein the nanoparticles have a zeta potential of −50 to 50 millivolts.

20. The method of claim 16, wherein the nanoparticles have a mean particle size ranging from 30 nm to 250 nm.

21. The method of claim 16, wherein the nanoparticles are suspended in a liquid medium.

22. A water-in-oil emulsion (W/O) comprising the composition of claim 1.

23. A water-in-oil-in water double emulsion (W/O/W) comprising the composition of claim 1.

24. A glass container comprising the composition of claim 1, or the stable aqueous suspension comprising the composition of claim 1.

25. The composition of claim 1, wherein the nanoparticles have a zeta potential of −50 mV to 50 mV.

* * * * *